(12) United States Patent
Murthy et al.

(10) Patent No.: US 12,157,901 B2
(45) Date of Patent: Dec. 3, 2024

(54) DENDRITIC CELL GENERATOR

(71) Applicant: Northeastern University, Boston, MA (US)

(72) Inventors: Shashi K. Murthy, Newton, MA (US); Bradley B. Collier, Jamaica Plain, MA (US)

(73) Assignee: Northeastern University, Boston, MA (US)

( * ) Notice: Subject to any disclaimer, the term of this patent is extended or adjusted under 35 U.S.C. 154(b) by 0 days.

(21) Appl. No.: 18/061,732

(22) Filed: Dec. 5, 2022

(65) Prior Publication Data
US 2023/0107804 A1    Apr. 6, 2023

Related U.S. Application Data

(63) Continuation of application No. 16/905,615, filed on Jun. 18, 2020, now Pat. No. 11,566,224, which is a
(Continued)

(51) Int. Cl.
*C12N 5/0784* (2010.01)
*C07K 14/525* (2006.01)
(Continued)

(52) U.S. Cl.
CPC .......... *C12N 5/0639* (2013.01); *C07K 14/525* (2013.01); *C07K 14/535* (2013.01);
(Continued)

(58) Field of Classification Search
CPC ...... C12N 5/0639; C12N 5/0018; C12M 1/22; C12M 23/16; C12M 23/42; C12M 25/02;
(Continued)

(56) References Cited

U.S. PATENT DOCUMENTS 10,731,131 B2    8/2020    Murthy et al.
11,566,224 B2    1/2023    Murthy et al.
(Continued)

FOREIGN PATENT DOCUMENTS

AU    2012205259 A1    8/2012
CA        2905786 A1    10/2014
(Continued)

OTHER PUBLICATIONS

International Search Report and Written Opinion for Int'l Appl. PCT/US16/40042, filed Jun. 29, 2016, entitled "Dendritic Cell Generator." dated Oct. 4, 2016.
(Continued)

*Primary Examiner* — Michael L Hobbs
(74) *Attorney, Agent, or Firm* — Hamilton, Brook, Smith & Reynolds, P.C.

(57) ABSTRACT

Devices, systems, and methods can be used for the automated production of dendritic cells (DC) from dendritic cell progenitors, such as monocytes obtained from peripheral blood. The invention makes it possible to obtain sufficient quantities of a subject's own DC for use in preparing and characterizing vaccines, for activating and characterizing the activation state of the subject's immune response, and to aid in preventing and/or treating cancer or infectious disease.

20 Claims, 20 Drawing Sheets

Related U.S. Application Data continuation of application No. 15/736,257, filed as application No. PCT/US2016/040042 on Jun. 29, 2016, now Pat. No. 10,731,131.

(60) Provisional application No. 62/185,906, filed on Jun. 29, 2015.

(51) Int. Cl.

| | |
|---|---|
| C07K 14/535 | (2006.01) |
| C07K 14/54 | (2006.01) |
| C07K 14/545 | (2006.01) |
| C12M 1/00 | (2006.01) |
| C12M 1/12 | (2006.01) |
| C12M 1/22 | (2006.01) |
| C12M 3/00 | (2006.01) |
| C12M 3/06 | (2006.01) |
| C12N 5/00 | (2006.01) |
| A61K 39/00 | (2006.01) |

(52) U.S. Cl.
CPC ...... *C07K 14/5406* (2013.01); *C07K 14/5412* (2013.01); *C07K 14/545* (2013.01); *C12M 1/22* (2013.01); *C12M 23/16* (2013.01); *C12M 23/42* (2013.01); *C12M 25/02* (2013.01); *C12M 29/10* (2013.01); *C12M 41/14* (2013.01); *C12N 5/0018* (2013.01); *A61K 39/00* (2013.01)

(58) Field of Classification Search
CPC ..... C12M 29/10; C12M 41/14; C07K 14/525; C07K 14/5406; C07K 14/5412; C07K 14/545; A61K 39/00
See application file for complete search history.

(56) References Cited

U.S. PATENT DOCUMENTS

| | | |
|---|---|---|
| 2005/0003533 A1 | 1/2005 | Kalinski |
| 2006/0115893 A1 | 6/2006 | Kobayashi et al. |
| 2007/0161051 A1 | 7/2007 | Tsinberg et al. |
| 2014/0065660 A1 | 3/2014 | Kim et al. |
| 2014/0193374 A1 | 7/2014 | Zhao et al. |
| 2018/0171296 A1 | 6/2018 | Murthy et al. |
| 2020/0385678 A1 | 12/2020 | Murthy et al. |

FOREIGN PATENT DOCUMENTS

| | | | |
|---|---|---|---|
| EP | 1 392 814 B1 | 6/2007 | |
| JP | 2010200693 A | 9/2010 | |
| WO | WO-03010292 A2 * | 2/2003 | ........... C12N 5/0087 |
| WO | 2017/004169 A1 | 1/2017 | |

OTHER PUBLICATIONS

Extended European Search Report for corresponding European Application No. 16818659.1, entitled "Dendritic Cell Generator," dated Feb. 22, 2019.

International Preliminary Report on Patentability for Int'l Appl. PCT/US16/40042, filed Jun. 29, 2016, entitled "Dendritic Cell Generator." dated Jan. 2, 2018.

* cited by examiner

FIG. 11B

DENDRITIC CELL GENERATOR

RELATED APPLICATIONS

This application is a continuation of U.S. application Ser. No. 16/905,615, filed Jun. 18, 2020, which is a continuation of U.S. application Ser. No. 15/736,257, filed Dec. 13, 2017, now U.S. Pat. No. 10,731,131, which is the U.S. National Stage of International Application No. PCT/US2016/040042, filed on Jun. 29, 2016, published in English, which claims the benefit of U.S. Provisional Application No. 62/185,906, filed on Jun. 29, 2015. The entire teachings of the above applications are incorporated herein by reference.

STATEMENT REGARDING FEDERALLY SPONSORED RESEARCH OR DEVELOPMENT

The invention was made with government support under AI118665 awarded by the National Institutes of Health. The government has certain rights in the invention.

BACKGROUND

Dendritic cells are antigen presenting cells that process antigens and present them on their surfaces for recognition by T cells, which then develop an active immune response. Dendritic cells are useful in therapeutic vaccines and in vitro methods for stimulating the immune system to attack pathogens and cancer cells, as well as to characterize immune responses, such as by assessing the activation state of CD4 cells in vaccination and infection.

Most dendritic cells are found in body tissues, with only a small number found in the circulation. Therefore, there is a need to generate patient-specific dendritic cells (DC), such as by the in vitro differentiation of CD14+ circulating monocytes (MC), which are a subset of peripheral blood mononuclear cells (PBMC). A common method of obtaining DC is via conversion of CD14+ MC to DC by a series of incubations with of cytokines carried out with manual intervention in multiple steps over a period of 5-10 days. There is a need for automated and scalable methods for generating DC from MC and for devices and systems to carry out such methods.

SUMMARY OF THE INVENTION

The invention provides methods, devices, systems, and kits for the isolation of monocytes (MC) from circulating blood of a subject and their conversion into dendritic cells (DC). Fluidic devices and systems of the invention permit patient-specific DC generation. Methods of the invention include an automated 6-step method that simplifies and shortens the process of generating DC. The devices and methods of the invention improve the utilization of patient blood samples for vaccine trials and reduce costs associated with DC production. The obtained DC can be utilized to study polyclonal T cell responses induced by infection or vaccination, to expand epitope-specific T cells, and with GMP protocols can be used to prepare DC vaccines for human use. DC represent about 1% or less of circulating PBMC, and thus large blood volumes are currently required to purify sufficient numbers for ex vivo use. In some embodiments, the methods, devices, and systems of the invention allow about 10-fold more DC to be generated/mL of blood, while substantially reducing costs by minimizing the consumption of expensive cytokine reagents.

In some embodiments, a DC generation system of the invention accepts whole human blood or a fraction thereof enriched in PBMC, isolates CD14+ monocytes therefrom, and mediates their conversion to DC via incubation with IL4 and GM-CSF for 2-6 days, followed by incubation with a maturation cocktail (e.g., containing IL1β, IL6, TNFα, and PGE2) for 1-3 days. In some embodiments, the system of the present technology is a 6-step process. In some embodiments, the DC generated by the system characterized via flow cytometry. In some embodiments, the system includes an automated flow control with user interface. In some embodiments, the system includes an integrated and. automated system that performs one or more of the flowing non-limiting functions: accepting a whole blood or PBMC sample, isolating monocytes, converting the monocytes into DC, and exposing the DC to antigen.

One aspect of the invention is a dendritic cell differentiation cassette. The cassette includes: a plastic body containing a cell culture chamber with a monocyte-binding substrate; a fluid inlet port; and a fluid outlet port. The plastic body, the fluid inlet port, and the fluid outlet port are fluidically coupled to the cell culture chamber and configured to provide flow of a liquid culture medium across the monocyte-binding substrate from the inlet port to the outlet port.

Another aspect of the invention is a dendritic cell generation system, which includes: one or more dendritic cell differentiation cassettes as described above; a culture medium reservoir fluidically coupled to the fluid inlet port of the one or more dendritic cell differentiation cassettes; a fluid collection reservoir fluidically coupled to the fluid outlet port of the one or more dendritic cell differentiation cassettes; and a pump configured for pumping fluid from the culture medium reservoir, through the cell culture chamber of the one or more dendritic cell differentiation cassettes, and into the fluid collection reservoir.

A further aspect of the invention is a cell culture system that includes: one or more fluid reservoirs; a pump operably coupled to the one or more fluid reservoirs; and a cell culture chamber fluidically coupled to the one or more fluid reservoirs. The cell culture chamber includes a fluidic channel having an inlet, an outlet, and a cell binding surface. The chamber is configured such that the fluidic channel is elevated in a manner that the inlet is below the outlet.

Yet another aspect of the invention is a cell culture system containing: a fluid reservoir configured for exchange of a gas from a fluid in the fluid reservoir into an external environment; a cell culture chamber comprising a fluidic channel that is configured to prevent gas exchange within the cell culture chamber; and a pump. The system is configured such that the pump pumps fluid from the fluid reservoir through the fluidic channel of the cell culture chamber.

Still another aspect of the invention is a cell culture system including: one or more fluid reservoirs; a pump operably coupled to the one or more fluid reservoirs; and a cell culture chamber fluidically coupled to the one or more fluid reservoirs. The cell culture chamber contains a fluidic channel having an inlet, an outlet, a first surface containing a first material to which cells bind, and a second surface containing a second material to which cells do not bind.

Even another aspect of the invention is a method of preparing dendritic cells of a subject. The method includes the steps of: providing the dendritic cell generation system described above and a liquid sample containing monocytes of the subject; pumping the liquid sample into the cell culture chamber of a dendritic cell differentiation cassette of the dendritic cell generation system, whereby at least a portion of the monocytes bind to the monocyte binding substrate of the cell culture chamber; pumping a dendritic cell differentiation medium into the cell culture chamber, whereby at least a portion of the bound monocytes differentiate into dendritic cells and detach from the monocyte-binding substrate; optionally pumping a dendritic cell maturation medium into the cell culture chamber to replace the dendritic cell differentiation medium, whereby at least a portion of the differentiated dendritic cells mature into mature dendritic cells; and optionally collecting mature dendritic cells from the cell culture chamber.

Another aspect of the invention is a method for dendritic cell generation. The method includes: providing a cell culture chamber containing a fluidic channel; introducing monocytes into the fluidic channel; and flowing a fluid through the fluidic channel such that a flow rate of the fluid through the fluidic channel is less than a sedimentation rate of the monocytes within the fluidic channel, thereby maintaining the monocytes within the fluidic channel without use of filters.

Still another aspect of the invention is another method for dendritic cell generation. The method includes: providing a cell culture chamber containing a fluidic channel; introducing monocytes into the fluidic channel; and flowing a culturing fluid through the fluidic channel in order to transform the monocytes into dendritic cells, wherein the method is conducted without using more than 25 milliliters of the culturing fluid.

Yet another aspect of the invention is a dendritic cell vaccine containing dendritic cells prepared by a method described above.

A further aspect of the invention is a kit for generating dendritic cells. The kit contains one or more dendritic cell differentiation cassettes as described above, a dendritic cell differentiation medium, and optionally a dendritic cell maturation medium.

Even another aspect of the invention is a method of fabricating the dendritic cell differentiation cassette as described above. The method includes the steps of: providing a polystyrene slab, first and second slabs of a thermoplastic material, a double-sided adhesive film; and two Luer fittings; forming a cell culture chamber slab from the first slab of thermoplastic material; forming the double-sided adhesive film into two adhesive layers, each corresponding to a shape of the cell culture slab; joining the cell culture chamber slab to the polystyrene slab using one of the adhesive films; joining the cell culture chamber slab to the second slab of thermoplastic material using the other adhesive film forming a sealed cell culture chamber; and mounting the Luer fittings on the second thermoplastic slab to form the fluid inlet and outlet ports of the cassette.

The invention can be further summarized by the following list of embodiments:

1. A dendritic cell differentiation cassette comprising:
   (i) a plastic body comprising a cell culture chamber, the chamber comprising a monocyte-binding substrate;
   (ii) a fluid inlet port; and
   (iii) a fluid outlet port;
   wherein the plastic body, the fluid inlet port, and the fluid outlet port are fluidically coupled to the cell culture chamber and configured to provide flow of a liquid culture medium across the substrate from the inlet port to the outlet port.

2. The dendritic cell differentiation cassette of embodiment 1, wherein the monocyte-binding substrate comprises a polystyrene surface that binds monocytes but not differentiated dendritic cells.

3. The dendritic cell differentiation cassette of embodiment 1 or embodiment 2, wherein the monocyte-binding substrate comprises a CD14 antibody.

4. The dendritic cell differentiation cassette of any of the preceding embodiments, wherein the monocyte-binding substrate forms a bottom of the cell culture chamber and comprises a flat surface.

5. The dendritic cell differentiation cassette of any of the preceding embodiments, wherein the cell culture chamber has an oval or rounded rectangular profile with curved walls and no corners in the profile.

6. The dendritic cell differentiation cassette of any of the preceding embodiments, wherein the fluid inlet port and fluid outlet port are disposed at opposite ends of the cell culture chamber.

7. The dendritic cell differentiation cassette of any of the preceding embodiments, wherein each of the fluid inlet port and fluid outlet port comprises a Luer lock fitting.

8. The dendritic cell differentiation cassette of any of the preceding embodiments, that is assembled from a polystyrene bottom slab and a poly(methyl methacrylate) (PMMA) top slab, the top and bottom slabs separated by a PMMA cell culture chamber slab.

9. The dendritic cell differentiation cassette of any of the preceding embodiments, that is configured to provide perfusion of adhered cells in the cell culture chamber at a shear stress of 0.1 dyne/cm$^2$ or less.

10. The dendritic cell differentiation cassette of any of the preceding embodiments, wherein the monocyte binding surface has a surface area from about 2 cm$^2$ to about 100 cm$^2$.

11. The dendritic cell differentiation cassette of embodiment 1, wherein the cell culture chamber has a height from about 0.1 mm to about 2 mm.

12. A dendritic cell generation system comprising:
   (i) one or more dendritic cell differentiation cassettes of embodiment 1;
   (ii) a culture medium reservoir fluidically coupled to the fluid inlet port of the one or more dendritic cell differentiation cassettes;
   (iii) a fluid collection reservoir fluidically coupled to the fluid outlet port of the one or more dendritic cell differentiation cassettes; and
   (iv) a pump configured for pumping fluid from the culture medium reservoir, through the cell culture chamber of the one or more dendritic cell differentiation cassettes, and into the fluid collection reservoir.

13. The dendritic cell generation system of embodiment 12, wherein the pump mechanism comprises a pump built into each of the one or more dendritic cell differentiation cassettes.

14. The dendritic cell generation system of embodiment 12, wherein the pump mechanism comprises one or more pumps detached from the one or more dendritic cell differentiation cassettes.

15. The dendritic cell generation system of any of embodiments 12-14, wherein the culture medium reservoir and/or fluid collection reservoir are built into each of the one or more dendritic cell differentiation cassettes.

16. The dendritic cell generation system of any of embodiments 12-14, wherein the culture medium reservoir and/or fluid collection reservoir are detached from the one or more dendritic cell differentiation cassettes.

17. A cell culture system comprising:
   (i) one or more fluid reservoirs;
   (ii) a pump operably coupled to the one or more fluid reservoirs; and (iii) a cell culture chamber fluidically coupled to the one or more fluid reservoirs, wherein the cell culture chamber comprises a fluidic channel having an inlet, an outlet, and a cell binding surface, and wherein the chamber is configured such that the fluidic channel is elevated in a manner that the inlet is below the outlet.

18. A cell culture system comprising:
    (i) a fluid reservoir configured for exchange of a gas from a fluid in the fluid reservoir into an external environment;
    (ii) a cell culture chamber comprising a fluidic channel that is configured to prevent gas exchange within the cell culture chamber; and
    (iii) a pump, wherein the system is configured such that the pump pumps fluid from the fluid reservoir through the fluidic channel of the cell culture chamber.

19. A cell culture system comprising:
    (i) one or more fluid reservoirs;
    (ii) a pump operably coupled to the one or more fluid reservoirs; and
    (iii) a cell culture chamber fluidically coupled to the one or more fluid reservoirs, wherein the cell culture chamber comprises a fluidic channel having an inlet, an outlet, a first surface comprising a first material to which cells bind, and a second surface comprising a second material to which cells do not bind.

20. The dendritic cell generation system of any of embodiments 12-16, or the cell culture system of any of embodiments 17-19, wherein the pump is a peristaltic pump, syringe pump, or a pressurized gas source.

21. The dendritic cell generation system of any of embodiments 12-16, or the cell culture system of any of embodiments 17-19, further comprising one or more structures selected from the group consisting of valves, additional fluid reservoirs, vents, additional fluid ports, sensors, switches, batteries, covers, optically transparent windows, imaging devices, and optical elements.

22. The dendritic cell generation system of any of embodiments 12-16, or the cell culture system of any of embodiments 17-19, further comprising one or more of the group consisting of a processor, a memory, a display, and a wireless transceiver.

23. The dendritic cell generation system or cell culture system of embodiment 22 comprising a processor, a memory, and a set of instructions executable by the processor for carrying out the method of any of embodiments 29-42.

24. The dendritic cell generation system or cell culture system of embodiment 22 comprising a processor, memory, and wireless transceiver, the system further comprising an app for a computer or cell phone, the app configured to send and receive information to and from the system.

25. The dendritic cell generation system or cell culture system of embodiment 24 that allows a user to remotely set flow rate, solution pumped through the cell culture chamber, valve and/or pump settings, or that allows a user to view an image of cells in the cell culture chamber, and/or obtain sensor information.

26. The dendritic cell generation system of any of embodiments 12-16, or the cell culture system of any of embodiments 17-19, further comprising a cell culture medium contained in a reservoir.

27. The dendritic cell generation system of any of embodiments 12-16, or the cell culture system of any of embodiments 17-19, which is configured as a single disposable unit.

28. The dendritic cell generation system of any of embodiments 12-16, or the cell culture system of any of embodiments 17-19, which is configured for operation within a cell culture incubator.

29. A method of preparing dendritic cells of a subject, the method comprising the steps of:
    (a) providing the dendritic cell generation system of any of embodiments 12-16 and a liquid sample comprising monocytes of the subject;
    (b) pumping the liquid sample into the cell culture chamber of a dendritic cell differentiation cassette of the system, whereby at least a portion of said monocytes bind to the monocyte binding substrate of the cell culture chamber;
    (c) pumping a dendritic cell differentiation medium into the cell culture chamber, whereby at least a portion of the bound monocytes differentiate into dendritic cells and detach from the monocyte-binding substrate;
    (d) optionally pumping a dendritic cell maturation medium into the cell culture chamber to replace the dendritic cell differentiation medium, whereby at least a portion of the differentiated dendritic cells mature into mature dendritic cells; and
    (e) optionally collecting mature dendritic cells from the cell culture chamber.

30. The method of embodiment 29, wherein the mature dendritic cells are Lin- and CD4+.

31. The method of embodiment 29, wherein the dendritic cell differentiation medium comprises IL4 and GM-CSF.

32. The method of embodiment 31, wherein said dendritic cell differentiation medium is pumped through the cell culture chamber continuously for about 2-6 days at a flow rate from about 1 μL/min to about 10 μL/min.

33. The method of embodiment 29, wherein the dendritic cell maturation medium comprises IL1β, IL6, TNFa, and PGE2.

34. The method of embodiment 33, wherein said dendritic cell maturation medium is pumped through the cell culture chamber continuously for about 1-3 days at a flow rate from about 1 μL/min to about 10 μL/min.

35. The method of embodiment 29, further comprising:
    (f) exposing the mature dendritic cells obtained in step (e) to one or more antigens.

36. A method for dendritic cell generation, the method comprising:
    (a) providing a cell culture chamber comprising a fluidic channel;
    (b) introducing monocytes into the fluidic channel; and
    (c) flowing a fluid through the fluidic channel such that a flow rate of the fluid through the fluidic channel is less than a sedimentation rate of the monocytes within the fluidic channel, thereby maintaining the monocytes within the fluidic channel without use of filters.

37. A method for dendritic cell generation, the method comprising:
    (a) providing a cell culture chamber comprising a fluidic channel;
    (b) introducing monocytes into the fluidic channel; and
    (c) flowing a culturing fluid through the fluidic channel in order to transform the monocytes into dendritic cells, wherein the method is conducted without using more than 25 milliliters of the culturing fluid.

38. The method of any of embodiments 29-37, wherein the liquid sample or the monocytes are provided as whole blood or a solution comprising leukocytes obtained by leukapheresis of the subject's blood.

39. The method of any of embodiments 29-38, wherein the subject or a source of the monocytes is a human or other mammal.

40. The method of any of embodiments 29-39, wherein dendritic cells from a single subject are prepared.

41. The method of any of embodiments 29-40, wherein dendritic cells from two or more subjects are prepared simultaneously.

42. The method of any of embodiments 29-41, wherein at least about 20%, 30%, 40%, 50%, 60%, 70%, 80%, or 90% of monocytes contained in the liquid sample are differentiated into dendritic cells and collected as dendritic cells.

43. A dendritic cell vaccine comprising dendritic cells prepared by the method of any of embodiment 29-42.

44. A kit for generating dendritic cells, the kit comprising:
   (i) one or more dendritic cell differentiation cassettes of any of embodiments 1-11;
   (ii) a dendritic cell differentiation medium; and
   (iii) optionally a dendritic cell maturation medium.

45. The kit of embodiment 44, wherein the dendritic cell differentiation medium comprises IL4 and GM-CSF and/or the dendritic cell maturation medium comprises IL1β, IL6, TNFa, and PGE2.

46. A method of fabricating the dendritic cell differentiation cassette of any of embodiments 1-11, the method comprising the steps of:
   (a) providing a polystyrene slab, first and second slabs of a thermoplastic material, a double-sided adhesive film; and two Luer fittings;
   (b) forming a cell culture chamber slab from the first slab of thermoplastic material;
   (c) forming the double-sided adhesive film into two adhesive layers, each corresponding to a shape of the cell culture slab;
   (d) joining the cell culture chamber slab to the polystyrene slab using one of the adhesive films;
   (e) joining the cell culture chamber slab to the second slab of thermoplastic material using the other adhesive film forming a sealed cell culture chamber; and
   (f) mounting the Luer fittings on the second thermoplastic slab to form the fluid inlet and outlet ports of the cassette.

BRIEF DESCRIPTION OF THE DRAWINGS

FIGS. 11A-11D show heat maps for the top most altered genes directly ex vivo comparing pre-vaccination and day 7 post-vaccination (peak of T cell activation) responses, for PO and ID BCG groups separately. BCG vaccination reproducibly altered expression patterns similarly across individuals within each group. The Venn diagram comparing the unique gene lists identified on day 7 post-vaccination (FIG.

11B), demonstrates that PO and ID BCG induced distinct activation patterns. FIG. 11C shows heat maps for the top most altered genes after BCG re-stimulation comparing pre-vaccination and day 56 post-vaccination (memory/effector responses), for PO and ID BCG groups separately. The Venn diagram comparing the unique gene lists identified on day 56 post-vaccination (FIG. 11D) demonstrates that PO and ID BCG induced distinct memory patterns. Preliminary GSEA analysis indicated that a set of asthma-associated genes were enriched in PO BCG recipients at both day 7 and 56.

DETAILED DESCRIPTION OF THE INVENTION

The present invention provides devices, systems, and methods for the automated production of dendritic cells (DCs) from dendritic cell progenitors, such as monocytes obtained from peripheral blood. The invention makes it possible to obtain sufficient quantities of a subject's own DCs for use in preparing and characterizing vaccines, for activating and characterizing the activation state of the subject's immune response, and to aid in preventing and/or treating cancer or infectious disease.

The invention makes it possible to automate as well as to remotely monitor and control methods of DC differentiation and maturation. The methods, devices, and systems of the invention can be scaled up to provide a large number of DCs, and can be operated either for a single subject, several subjects in parallel (whereby their cells and the progeny thereof remain separate), or for several pooled subjects (whereby their cells and progeny thereof are pooled together). Compared to prior art methods and devices, the methods and devices of the invention are simple and efficient, reducing the costs of expensive reagents (e.g., cell culture media and cytokines) to a minimum.

The invention makes available a ready supply of a patient's own DCs, which have many uses. For example, the patient's own DCs can be used to produce customized DC vaccines for combatting a cancer or infectious disease of the patient. A patient's own DCs also can be used to provide a supply of activated DCs suitable for introduction into the patient. The patient's own DCs can be activated in vitro by exposure to one or more antigens, and the activated DCs can be used to activate T cells of the patient, either in vitro or by introducing the activated DCs into the patient. Thus, the DCs produced by the invention can be used to improve vaccine development. The devices of the invention also can be used to optimize DC differentiation and maturation protocols from monocytes or other types of DC progenitor cells.

Figures 1A, 1B:
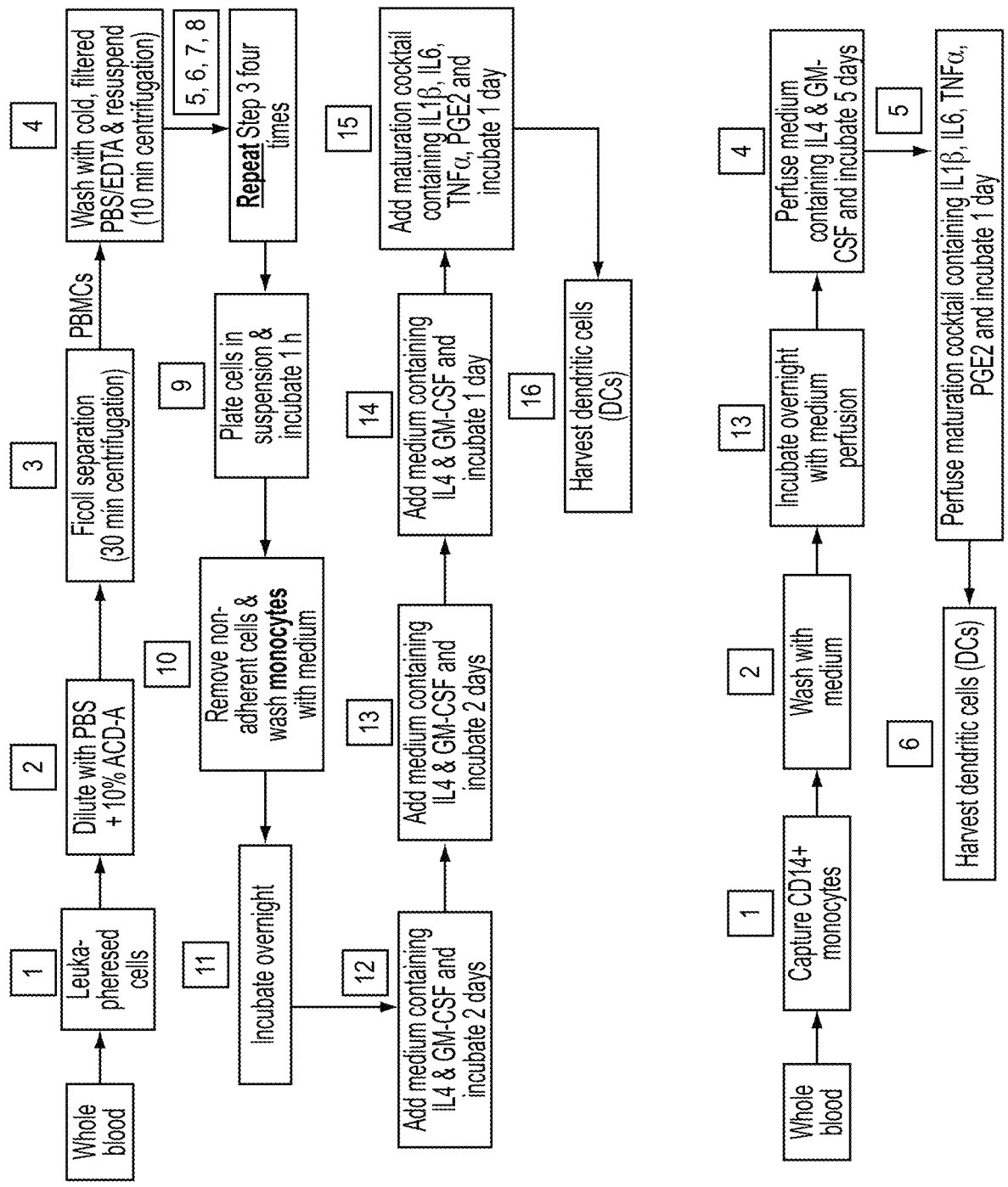
FIG. 1A is a flow chart showing the steps in a prior art method for producing dendritic cells from peripheral blood monocytes.
FIG. 1B is a flow chart showing an embodiment of a method of the present invention for generating dendritic cells.

The method of generating DCs from PBMCs of the present invention is far simpler and more efficient than methods of the prior art. FIG. 1A shows a representative prior art method, which relies on culturing monocytes (MCs) on 6-well plates and the use of multiple manual steps. The method requires 8 steps just to produce PBMCs from whole blood, ready for plating. Following the adherence of MCs, several changes of culture medium are required to differentiate and mature the DCs. In contrast, a method of the invention, which is represented in FIG. 1B, leads to the binding of MCs from whole blood in just one step, and produces matured DCs in a total of six steps, with a minimum of user intervention.

In an embodiment of the invention, a method of preparing dendritic cells of a subject includes the step of selectively binding MCs. A liquid sample containing MCs of the subject is caused to flow into a cell culture chamber having a surface that selectively binds at least a portion of the monocytes. The surface can bind MCs because the surface contains receptors for ligands exposed on the surface of MCs (e.g. anti-CD14 antibody), or because the physical and/or chemical nature of the surface material allows the surface to selectively bind MCs while binding other PBMCs poorly or not at all. For example, in a preferred embodiment, the floor of the cell culture chamber, or a portion of a fluidic channel of a fluidic device, is formed of polystyrene, or coated with polystyrene, which has the property of selectively binding MCs but not other types of PBMCs. In another example, an anti-CD14 antibody is contained in an alginate gel coating a surface of a cell culture chamber or a fluidic chamber of a fluidic device. The MCs are captured within the gel by binding to the antibody, and can be released from the surface by dissolving the gel (e.g., by chelating $Ca^{2+}$ ions using EDTA). The use of selective binding of MCs avoids several steps and manipulations of a whole blood sample ordinarily used to purify MCs. Further, by binding MCs directly in a device that is subsequently used for their differentiation and maturation into DCs, yet additional steps of plating and transferring the cells can be eliminated, and recovery can be improved. The yield and purity of the MCs bound in this step should be optimized, and can each independently be about, or at least about, 20%, 25%, 30%, 35%, 40%, 45%, 50%, 60%, 70%, 80%, 90%, 95%, or 98%. Preferably, the method is carried out in a device that permits the generation of DCs with not more than 25 milliliters of the culturing fluid, so as to minimize consumption of expensive reagents.

The source of MCs is preferably a whole blood sample from a single subject, such as a single human or other mammalian subject. Limiting the sample to a single individual has the advantage that the DCs generated therefrom can be reintroduced into the individual for various vaccination or other strategies designed to enhance an immune response of the individual, without any risk of an immune reaction against the DCs. The whole blood sample can be, for example, 1, 2, 3, 5, 10, 20, 25, 30, 35, 40, 45, 50, 60, 70, 80, 90, or 100 mL of whole blood, and the sample can be drawn at once or at several different times and pooled. As an alternative to using a whole blood sample, the liquid sample containing MCs can be a PBMC preparation, such as one obtained from whole blood or by leukapheresis. The sample containing MCs also can be pooled from several different individual subjects, particularly if generation of a larger quantity of DCs is desired than can be provided by a sample from a single individual.

After MCs are selectively retained in the cell culture chamber, the chamber optionally can be washed with culture medium to remove unbound cells from the chamber. The culture medium for this and subsequent steps can be any standard or customized cell culture medium suitable for maintaining the viability of MCs and promoting their differentiation to DCs, as well as the maturation of DCs. A single medium can be used for all steps, with different cytokines or other factors added to promote maintenance, differentiation, and/or maturation, or different media can be used for different steps in the procedure. The washing can be performed, e.g., over several minutes to an hour, or up to several hours. Preferably, the washing is performed at a flow rate that is sufficiently slow as to allow the removal of unbound cells and other sample components (e.g. blood proteins and other molecular components, other cells, and thrombocytes). For example, with suitable fluidic device design and an appropriately selected pump setting, a flow rate can be achieved that allows unbound cells and molecular components to be washed away, while leaving bound MCs attached to the MC binding surface. Such a flow rate can be, for example, from about 0.1 μL/min to about 20 μL/min, or more preferably from about 1 μL/min to about 10 μL/min, or even from about 2 μL/min to about 5 μL/min.

Once MCs are at least partially purified and have adhered to the MC binding surface of the cell culture chamber or a suitable channel of a fluidic device, one or more cytokines can be added to the culture medium in order to cause differentiation of the MCs to DCs and to induce maturation of the DCs. This can be done in one or more steps, and if done in more than one step, the cytokine mixture can be varied from one step to the next. For example, in a preferred embodiment, the differentiation of MCs to DCs can be induced by replacing the MC washing or maintenance medium with a dendritic cell differentiation medium. In one such embodiment, the differentiation medium contains IL4 and/or GM-CSF, which serve to promote conversion of the bound MCs to DCs. The differentiation medium is left in place, or continuously perfused, or periodically replaced, over a period of time sufficient for the differentiation to occur in a portion, or in essentially all, of the MCs. For example, differentiation medium can be present for a number of days, such as 1, 2, 3, 4, 5, 6, 7, 8, 9, or 10 days, or 3-5 days, or 2-6 days, or 4-6 days, or 5-7 days, during which time MCs are converted into immature or mature DCs. The differentiation is preferably associated with changes in cell morphology that are characteristic of the DC phenotype, such as an increase in cell size and the appearance of branched cell surface dendrites or sheets. Changes in the cell surface morphology and protein expression of dendritic cells result in their non-adherence to the MC binding surface and their release therefrom.

In another preferred embodiment, after the MC have differentiated into DC, and the culture chamber or fluidic channel contains predominantly immature DC, the differentiation medium is replaced with a dendritic cell maturation medium that contains a different mixture of cytokines, one that promotes the maturation of DCs. For example, the DC maturation medium can contain a mixture of IL1β, IL6, TNFa, and PGE2. The DC maturation medium can be introduced as a replacement for the differentiation medium, or it can be continuously perfused or periodically replaced. The DC maturation medium can be present for a number of days, such as 0.5, 1, 2, 3, 4, 5, 6, or 7 days, or 1-3 days, 1-2 days, 2-4 days, 2-3 days, 3-5 days, or 3-4 days. In response thereto, at least a portion of the differentiated dendritic cells change their phenotype into that of mature dendritic cells. According to a preferred embodiment, dendritic cells are considered mature when they exhibit the phenotype Lin- and CD4+, which can be ascertained using flow cytometry or fluorescence activated cell sorting, together with suitable labeled antibodies. During this part of the process, the DCs are not attached to a surface, but remain in suspension in the medium contained within the cell culture chamber or fluidic channel. Care is taken to retain a slow flow rate that allows the suspended DCs to remain in place within the cell culture chamber or fluidic chamber, without being displaced into other parts of the dendritic cell generation system. That is, the flow rate of the fluid through the culture chamber or fluidic channel is less than the sedimentation rate of the cells in the medium. In this manner, the use of filters for maintaining cells within the system can be avoided; this is preferred because filters can damage or reduce the yield of MCs and/or DCs.

After DCs have matured within the cell culture chamber or fluidic channel, they can be harvested from the culture device and preserved (e.g., by freezing) or directly put to use, or can be allowed to remain within the culture device for further processing. For example, the mature DCs can be exposed to one or more antigens, pathogens, vectors, and the like in order to promote antigen processing and presentation on the DC cell surface. The mature DCs also can be co-incubated by T cells, such as by adding T cells to the cell culture chamber or fluidic channel, where the T cells can contact and interact with the DCs.

The invention also provides fluidic devices and systems for the automated or semi-automated collection and purification of MCs, differentiation of DCs, maturation of DCs, and other processes relating to DCs or other cell types. Two representative embodiments of fluidic devices for the capture of MCs and the generation of DCs are depicted in FIGS. 2A and 2E.

Figure 2A:
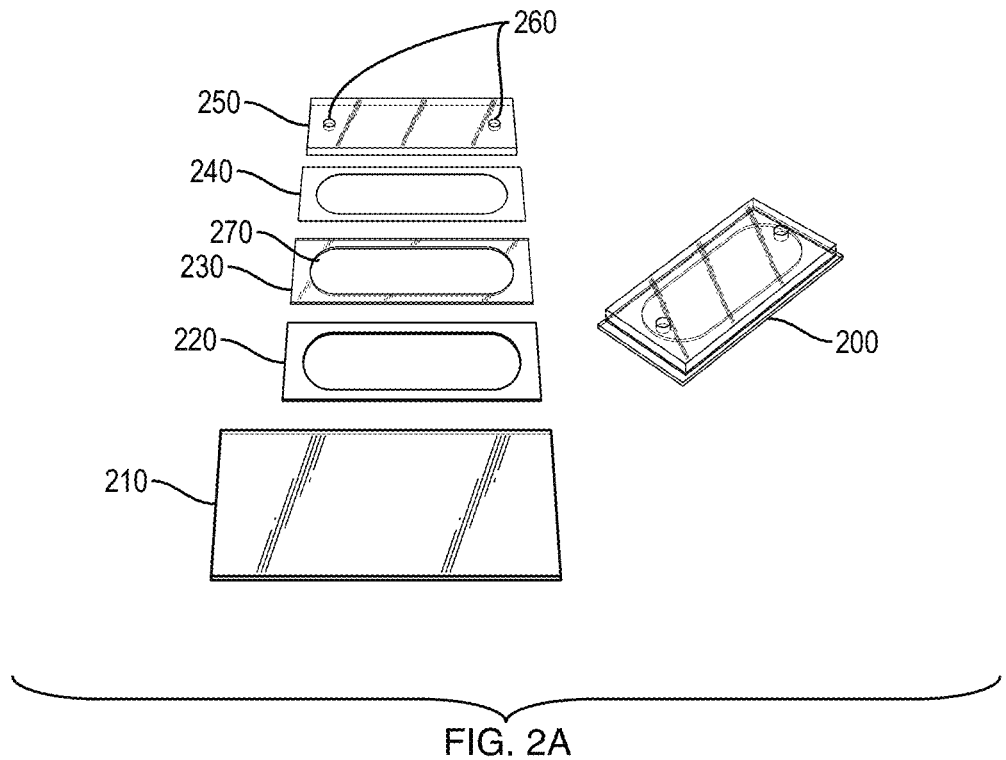
FIG. 2A, left hand side, is an illustration of the individual parts used to prepare a dendritic cell differentiation cassette of the present invention. The assembled dendritic cell differentiation cassette is shown at the right hand side of FIG. 2A, and in FIG. 2B in a top perspective view.
Figure 2B:
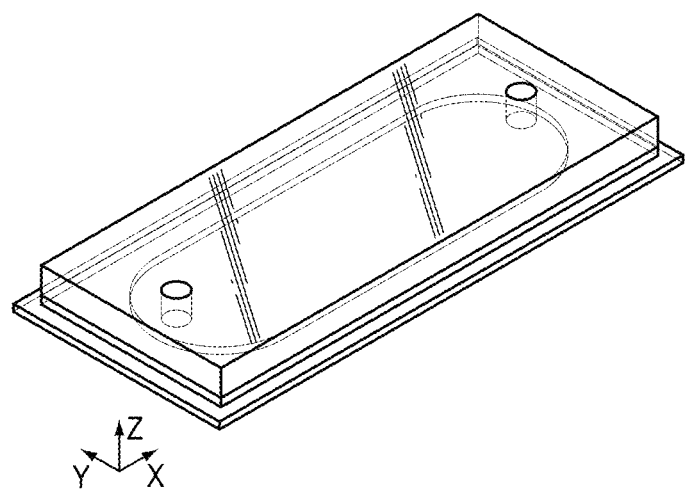
FIG. 2C shows a side view of the dendritic cell differentiation cassette of FIG. 2B.
FIG. 2D shows a top view of the same device. Dimensions shown in FIGS. 2C and 2D are in mm.
FIG. 2E shows a different embodiment of a dendritic cell differentiation cassette containing post structures within the cell culture chamber; the posts, together with the chamber floor, form the monocyte binding surface.
Figure 2C:
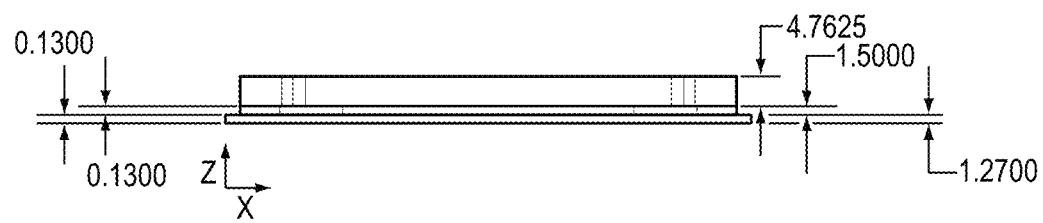
Figure 2D:
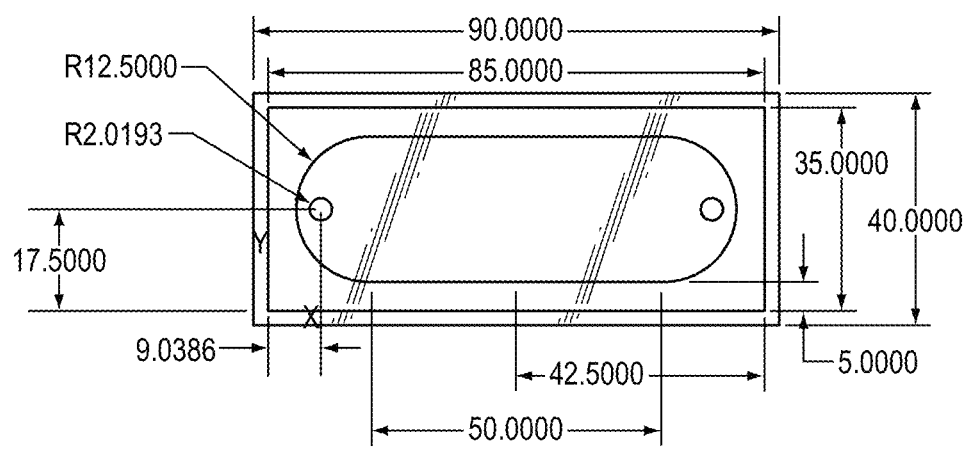
Figure 2E:
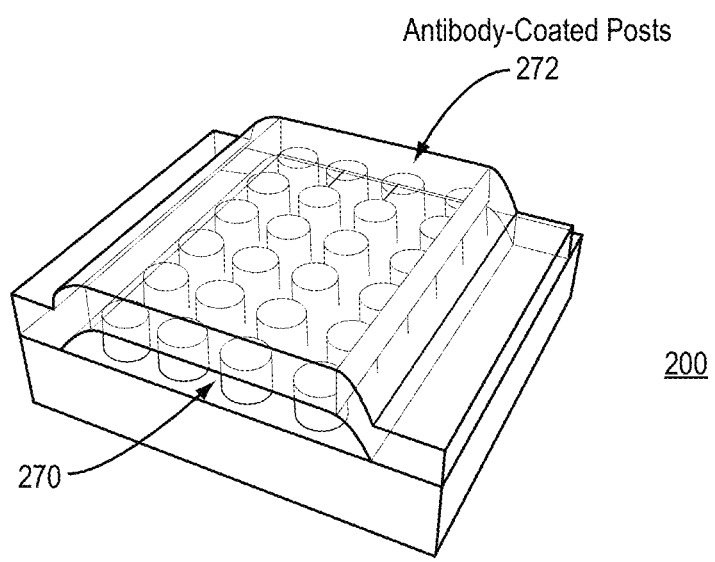

FIGS. 2A-2D show a preferred design of a dendritic cell differentiation cassette. Cassette 200 is built from the layers shown at the left side of FIG. 2A, which are assembled with the aid of double sided adhesive film. The design of the cassette allows it to receive a suitable volume of whole blood or another fluid sample containing MC, bind essentially all of the MCs contained in the sample. The cassette contains a cell culture chamber which forms the central open fluid space within the cassette. The floor of the chamber is, or contains as a portion thereof, a MC binding surface. The preferred geometry of the cell culture chamber is that of a flat, thin, space whose inner sides are all rounded and devoid of corners or vertices. An oval or rounded rectangular profile of the chamber is preferred. The flat surface and low height help to avoid turbulence that would lead to fluid shear stress, which would be disruptive to cells within the chamber and can reduce both cell viability and yield. Therefore, an important feature of the cassette is that it avoids or minimizes exposure of the cells within to shear stress. This is accomplished by the use of a flat surface with a minimum of protuberances or surface roughness, by the avoidance of sharp boundaries within the fluid pathway and within the cell culture chamber, by the use of laminar flow where possible (which is enhanced by keeping the cell culture chamber thin, such as from about 0.1 mm to about 2 mm in height), and by the inclusion of a bubble trap or gas venting mechanism for the elimination of gas bubbles during perfusion of the cell culture chamber. Both the achievement of laminar flow and the elimination of gas bubbles are promoted by the positioning of inlet and outlet ports at opposite sides of the cell growth chamber, such as shown in FIG. 2A. Further, the cassette can be mounted at an angle, with the outlet port positioned above the level of the inlet port, to assure that any bubbles entering the cell growth chamber through the inlet port are quickly eliminated at the outlet port by rising up to the outlet port, aided by their buoyancy.

Fluidic devices of the invention, including the dendritic cell differentiation cassette, or any cell growth or culture chamber, can be provided in either a microfluidic embodiment (i.e., wherein one or more channels or chambers therein has a dimension in the range of from about 1 μm to about 999 μm) or a microfluidic embodiment (wherein all of the channels or chambers therein have dimensions of about 1 mm or more. The fluidic devices can further include fluid reservoirs, additional fluid channels or compartments, gaskets or seals, mixing zones, valves, pumps, vents, channels for pressurized gas, electrical conductors, reagents, ports, and tubing as required by a particular design. They also may contain one or more control modules, transmitters, receivers, processors, memory chips, batteries, displays, buttons, controls, motors, pneumatic actuators, antennas, electrical connectors, and the like. The devices preferably contain only materials that are nontoxic to mammalian cells and that are compatible with sterilization by the use of alcohol and/or heat. Where needed, surfaces of the devices can be made more hydrophilic, such as by exposure to a plasma, or can be coated with one or more gels, chemical functionalization coatings, proteins, antibodies, glycoproteins, lipids, glycolipids, nucleic acids, proteoglycans, glycosaminoglycans, cytokines, or cells. The devices are also preferably compatible with use within a standard mammalian cell culture incubator, and in some embodiments do not allow the diffusion of gas through the material, as that could alter the composition of the culture medium within the device. Fluidic devices of the invention also are preferably modular and capable of fluidic connection to other similar devices either in series (i.e., with fluid flowing from one device into another) or in parallel, and may also be so configured as to physically stack with one another or be capable of physical arrangement within a related device such as an incubator, a pump, or a dendritic cell generation system. Fluidic devices of the invention are preferably devoid of fluid leaks under operating conditions and capable of sterile operation over a period of days to weeks.

While the configuration shown in FIGS. 2A-2D is preferred, other configurations are also contemplated. For example, in order to increase media exposure to adherent cells, the middle layer of the device (cell culture chamber slab) can be made very thin, even omitting the cell culture chamber slab and using only one double-sided adhesive layer rather than the adhesive/PMMA/adhesive that is depicted in FIG. 2A. Posts, such as shown in FIG. 2E (see structures 272), or other structures such as a sinusoidal channel or an array of chambers, can be included in the cell culture chamber in order to increase the surface area available for adhesion of cells, such as MCs. Vertical wells can be added to each side of the device by adding further layers to the device. Such vertical structures can be useful to trap cells that become non-adherent. A self-contained fluidic pump also can be included, especially in conjunction with one or more internal fluid reservoirs and valves, which can eliminate the need for an external pump and tubing as well as external culture medium reservoirs. Reservoirs for one or more cytokine stock solutions can also be included; if processor controlled valves are also included, this can avoid the need to switch the culture medium supply and thereby reduce or eliminate the chance of contamination.

Figure 3A:
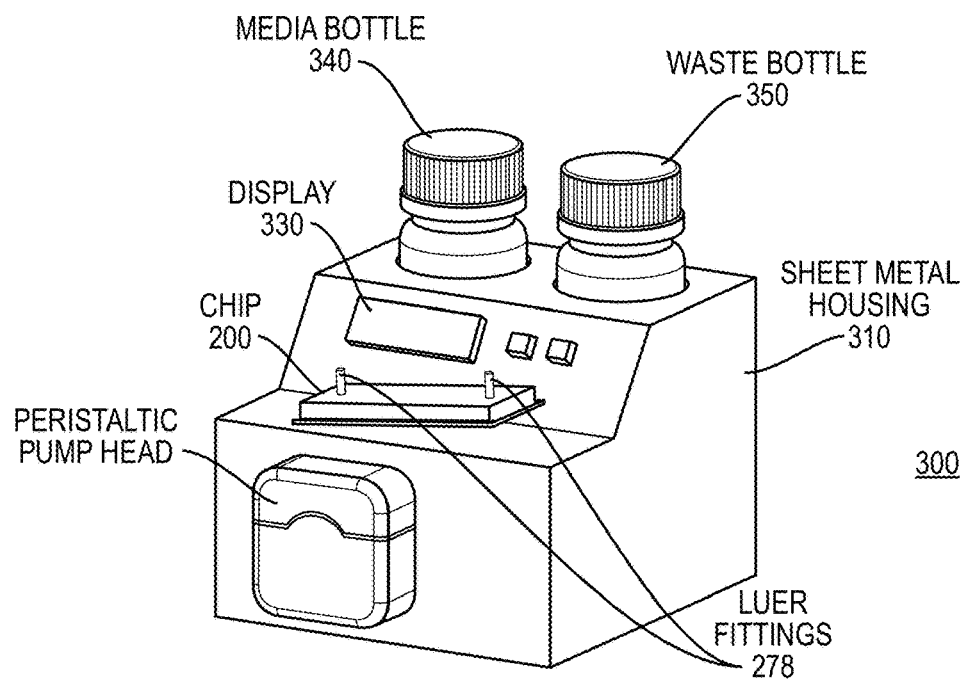
FIG. 3A shows an embodiment of a dendritic cell generation system according to the present invention.

A dendritic cell generation system of the invention includes at least a cell culture chamber, a pump, a culture medium reservoir, and fluidic connections between the medium reservoir, the pump, and the cell culture chamber. The system can also be provided without the cell culture chamber, which can be added to the system by the user, optionally together with one or more tubings for connecting the culture medium reservoir to the pump and DC differentiation cassette. The cell culture chamber can be provided as part of one or more dendritic cell differentiation cassettes as described above, or as one or more different structures. The culture medium reservoir can be provided as one or more capped bottles, each containing an inlet port and an outlet port, or an outlet port and a vent. a fluidically coupled to the fluid inlet port of the one or more dendritic cell differentiation cassettes; a fluid collection reservoir fluidically coupled to the fluid outlet port of the one or more dendritic cell differentiation cassettes; and a pump configured for pumping fluid from the culture medium reservoir, through the cell culture chamber of the one or more dendritic cell differentiation cassettes, and into the fluid collection reservoir. An embodiment of a DC generating system 300 is depicted in FIG. 3A. The system includes housing 310 with spaces for containing culture medium reservoir 340 and waste reservoir 350 (each the size and shape of commercially available glass or plastic culture medium bottles with plastic caps), a mounting area for DC differentiation cassette 200, an exposed peristaltic pump head configured for accepting peristaltic pump tubing leading from the culture medium bottle to the inlet port of the cassette (another tubing leading from the outlet port of the cassette to the waste bottle does not need to pass through the pump head), a display 330, and control buttons, knobs, or switches. This system can also include a heater (not shown) for controlling the temperature of the cassette and optionally the culture medium reservoir; in such a configuration, no incubator is required, and the system can operate autonomously, with only a source of electrical power. If the system lacks a heater, it can be operated inside of a cell culture incubator. Similar systems that include two or more cassettes and pump heads (e.g., one for each cassette, such as 2, 3, 4, 5, 6, 7 8, 9 10 or more cassettes and pump heads) are also contemplated. In such multi-cassette systems, the control electronics, display, and buttons, knobs, or switches can either be shared among the different cassettes, or duplicated with one set for each cassette.

The invention also provides kits for generating dendritic cells using the DC generating system. The kit can contain one or more dendritic cell differentiation cassettes, and a culture medium. Optionally, the kit can include a dendritic cell differentiation medium and/or a dendritic cell maturation medium instead of, or in addition to, the cell culture medium. The kit can also include stock solutions of one or more cytokines, such as IL4, GM-CSF, IL1β, IL6, TNFa, and/or PGE2. Optionally, the kit also can include a set of labeled antibodies for characterizing DCs by flow cytometry, and also can optionally include a sample of DCs for use as a standard.

EXAMPLES

Example 1. Fabrication of Dendritic Cell Differentiation Cassette

The dendritic cell differentiation cassette shown in FIGS. 2A-2D was fabricated for use with a variety of embodiments of the dendritic cell generation system of the invention, such as the embodiment shown in FIG. 3A. In this embodiment of the system, growth medium bottles having threaded access ports are utilized for the reservoir and waste containers to reduce the possibility of contamination during use. The monocyte binding surface area of the cassette's cell culture chamber was 17.41 $cm^2$, which was suitable for binding and differentiating monocytes contained in 25 mL of human blood. Silicone gaskets were cut to fit around the Luer connectors that are attached to the device; the gaskets prevent leaking through the tapped holes. The monocyte binding surface area of the cassette's cell culture chamber was 17.41 $cm^2$, which was suitable for binding and differentiating monocytes contained in 25 mL of human blood.

FIG. 2A shows a schematic representation of the components used to construct the cassette. The components are, from top to bottom: PMMA lid 250 with threaded holes 260 for addition of Luer lock fittings (shown as 278 in FIG. 3A), double-sided adhesive 240 (with liners still on), PMMA channel 230, double-sided adhesive 220 (with liners still on), and polystyrene bottom 210. The fluidic device was designed to carry out perfusion based cell culture, and was constructed using three layers of thermoplastic material joined by adhesive transfer tape. The part designs were created using CAD software and then transferred to a laser cutter which allowed the plastic and adhesive to be cut to the specified size and shape.

The bottom thermoplastic layer was made of clear 0.05" thick polystyrene that was cut into a rectangle shape slightly larger than the other layers to account for the melting and deformation that laser cutting causes in polystyrene. The polystyrene was then oxygen plasma treated to make the monocyte binding surface more hydrophilic (similar to treatment of standard polystyrene cell culture flasks). The second thermoplastic layer (cell culture chamber layer) was PMMA that was 1/16" thick. It was initially cleaned using a sonic toothbrush and Contrad 70 followed by rinsing with 70% ethanol. Then, one liner was removed from a section of adhesive tape which was the same size as the PMMA. The adhesive layer was then carefully applied to the PMMA. Bubbles were removed, and the pressure-sensitive adhesive was activated by applying force with a laminating roller. This process was repeated on the other side of the PMMA, such that the PMMA had a layer of adhesive (and liner) on each side of it. This adhesive coated plastic was then laser cut to create a fluidic channel (cell culture chamber). The top thermoplastic layer served as a cover to the fluidic channel and was made from 3/16 inch thick PMMA. In addition, the top layer served as the base for inlet and outlet fluidic connections. The connections were made by laser cutting through holes which were then tapped manually to provide 10-32 threads for accepting 10/32 male Luer fittings. Fluid was later introduced to the system by connecting the Luer adapter to a blunt dispensing needle with tubing pushed onto the blunt needle portion. The top PMMA and bottom polystyrene layers were cleaned the same way as described above for the PMMA middle layer. The three layers were then combined by removing the remaining liner layers on the adhesive layers above and below the middle cell culture chamber slab one at a time and applying to the top and bottom layers. As before, pressure was applied using a laminating roller to active the adhesive. All steps described above were performed in a biological safety cabinet where possible to reduce the possibility of biological contamination. Table 1 lists components of the device.

TABLE 1

| Supplier | Part # | Description | Materials | Autoclavab |
|---|---|---|---|---|
| Idex | P-301X | Flangeless Male Nut 1/4-28 Flat-Bottom for 1/8" OD | Delrin | yes |
| Idex | P-675 | 1/4-28 Female to Male Luer Assembly | Tefzel (EFTE), polypropylene | yes |
| Idex | P-300NX | Flangeless Ferrule Tefzel, 1/4-28 Flat-Bottom, for 1/8" OD Natural | Tefzel (EFTE) | yes |
| Cole Parmer | EW-45508-50 | Female luer × 1/16" hose barb, smooth bore | poylpropylene | yes |
| Cole Parmer | EW-45518-00 | Male luer with lock ring × 1/16" hose barb | polypropylene | yes |
| Cole Parmer | EW-95612-36 | Masterflex Tygon platinum cured silicone ext tubing, 1.52 mm ID | Silicone (platinum cured) | yes |
| Cole Parmer | EW-95713-12 | 2-Stop PharMed BPT Tubing, 0.25 mm | | yes |
| Cole Parmer | EW-45518-84 | Adapter, male luer lock to 10-32 thread | polypropylene | yes |
| Cole Parmer | EW-78001-20 | Ismatec IPC-N (ISM937C) Low-Speed Digital Peristaltic Pump; 12-Channel | | — |
| Fisher Scientific | 01-812-55 | Fisherbrand Instant Sealing Sterilization Pouches (7 × 13") | | yes |
| Fisher Scientific | 02-542A | Kimble KIMAX GL45 Media/Storage Bottles (100 mL) | | yes |
| Fisher Scientific | SLGP033RS | EMD Millipore Millex Sterile Syringe Filters: PES Membrane-Green (0.22 um) | | — |
| Fisher Scientific | 11-189-15G | Dow Corning Silastic Laboratory Tubing | Silastic | yes |
| Fisher Scientific | 50-634-365 | Cole Parmer Tubing PTFE 1/16 × 1/8" | PTFE | yes |
| McMaster-Carr | 5827T22 | NSF-Certified Silicone Rubber, 1/16" Thick, 12" × 12", Translucent | Silicone | yes |
| McMaster-Carr | 8560K171 | Optically Clear Cast Acrylic Sheet, 1/16" Thick, 12" × 12" | PMMA | no |
| Grainger | 15C893 | 3M 468MP Adhesive Transfer Tape, 12" × 12" | | |
| Dick Blick | 18908-1959 | Clear Styrene Sheet, 18" × 24", 0.05" thick | polystyrene | no |
| Component Supply | NE-301PL-C | Stainless Steel Blunt Needle with Luer, 30 gauge × 1/2" length | polypropylene, stainless steel | yes |
| CP Lab Safety | WF-GL45-4KIT | 4-Port Cap for Glass Bottles, GL45, Complete Kit | PTFE, polypropylene | yes |
| CP Lab Safety | WF-AQ-1-8 | 1/4-28 Threaded Tubing Adapter for 1/8" tubing | polypropylene, Tefzel | yes |
| CP Lab Safety | WF-1428-PLUG | 1/4-28 Plug | Teflon PFA | yes |
| Qosina | 11544 | Female Luer Lock to Barb Connector, 1/16" | polycarbonate | yes |
| Qosina | 11545 | Male Luer Lockto Barb Connector, 1/16" | polycarbonate | yes |
| Qosina | 12090 | Male to Male Luer Lock Connector | polypropylene | yes |
| Saint Gobain | AAD04091 | Tygon Tubing, ND-100-80, 0.01" ID, 0.03" OD | | |

Example 2. Dendritic Cell Generation System

Figure 3B:
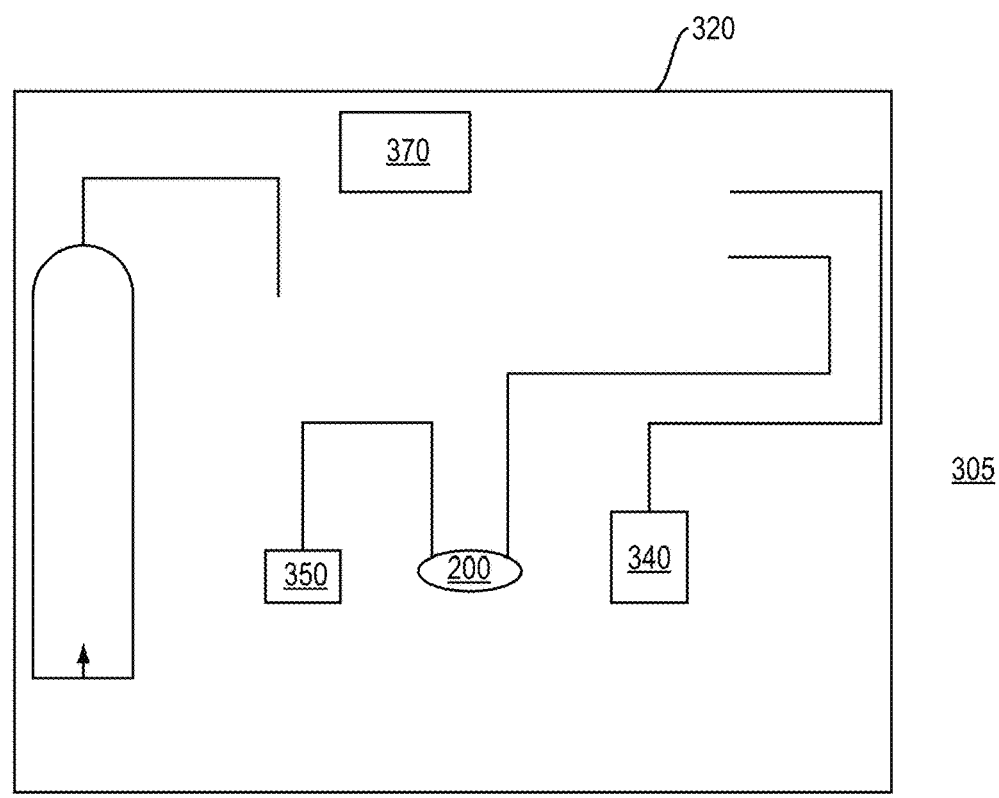
FIG. 3B shows a schematic illustration of another embodiment of a dendritic cell generation system according to the invention.
Figure 3C:
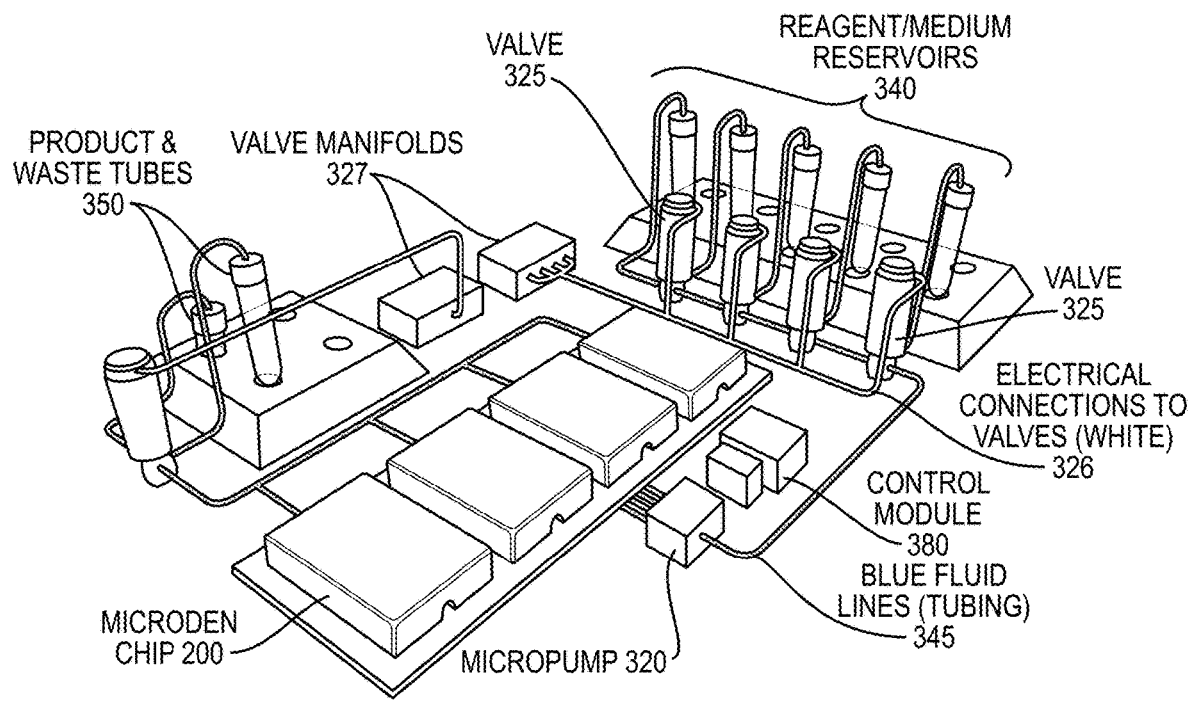
FIG. 3C shows a schematic illustration of yet another embodiment of a dendritic cell generation system.

A dendritic cell generating system as shown in FIG. 3B was set up. The system included the dendritic cell differentiation cassette described in Example 1 plus several other components. An ordinary mammalian cell culture incubator (maintained at 37° C., 5% $CO_2$, 95% humidity) was used to keep certain system components and the cells in the appropriate environment. Growth medium supply reservoir 340 and effluent collection reservoir 350 were kept in the incubator. These reservoirs consisted of 100 mL culture medium storage bottles. Four port (1/4-28 threaded) caps were attached to the bottles to allow fluid removal and gas exchange. On one port, a sterile syringe filter was attached using appropriate connectors. The filter allowed gas exchange to occur without risking contamination of the growth medium. On two other ports, tubing was inserted to allow the media to be pumped to the remaining system. The fourth port was plugged. In order to pump the media to the rest of the system, the culture medium reservoir was connected to a peristaltic pump located outside of the incubator, with supply tubing passed through an access port of the incubator. The medium was then pumped into the incubator to the dendritic cell differentiation cassette and out the incubator to the fluid collection reservoir, which was set up similar to the supply reservoir. Small diameter tubing was used to reduce heat exchange while the medium was transiting through the pump outside the incubator.

Example 3. Whole Blood Sample Preparation

Approximately 25 mL of whole blood was obtained from a human subject in 4 sodium heparin coated vacutainers with the assistance of a phlebotomist. A cell separation was then performed in a sterile manner using Ficoll-Paque PLUS according to the following protocol. The whole blood was first diluted two times with PBS containing 10% ACD-A (acid citrate dextrose). The blood solution was then carefully layered on top of 15 mL Ficoll solution in each of two 50 mL conical centrifuge tubes. The tubes were centrifuged at 500×g at 4° C. for 30 minutes, with the brake on the centrifuge turned off to prevent disturbing the cell pellet. Following centrifugation, the blood components had separated into three distinct regions. The buffy coat, consisting of peripheral blood mononuclear cells (PBMCs) was located just below the plasma layer at the top of the centrifuge tube. To remove the PBMCs, the plasma was removed and discarded until only ~1 cm of plasma remained. The PBMCs (with some plasma) from each tube were then transferred to new 50 mL tubes and diluted with cold (4° C.) PBS containing 1 mM EDTA to a total volume of 45 mL. The tubes were then centrifuged at 270×g for 10 min at 4° C. with the brake off. Following centrifugation, the supernatant was removed and the cells were combined into one tube and resuspended in cold PBS with 1 mM EDTA to a total volume of 45 mL. The cells are then centrifuged one final time at 130×g for 10 minutes at 4° C. with the brake set to a low value. After removing the supernatant, the cells were resuspended in 3 mL of dendritic cell conversion media and counted. A small aliquot (~0.25 mL) was removed for analysis by flow cytometer, while the remainder was diluted to the necessary concentration for cell seeding in a dendritic cell differentiation cassette. The cell concentration was approximately $2 \times 10^6$ cells/mL, but could also be diluted as low as $5 \times 10^5$ cells/mL if more volume was needed.

Example 4. Culturing of Monocytes

Prior to beginning cell culture experiments, all components that were not sterile as purchased were rinsed with 70% ethanol followed by sterile growth medium. The dendritic cell differentiation cassette was filled with culture medium and allowed to incubate for at least an hour in the incubator. During this time, the inlet and outlet connections on the device were closed. After removing the medium, about 3 mL of cell solution (see Example 3) were then added to the cassette, which was then incubated for an hour to allow monocytes to attach to the hydrophilic polystyrene surface. After an hour, the medium was poured out of the cassette, removing any non-adherent cells. The medium was replaced with fresh medium, and the device was connected to the rest of the system for perfusion. Fresh culture medium was perfused using a low flow rate of 2 µL/min until the end of the experiment.

Example 5. Cell Viability

The dendritic cell generation system of Example 2 was tested for their ability to keep cells alive using the LIVE/DEAD cell viability assay (Molecular Probes L3224). PBMCs were isolated using a Ficoll separation as in Example 3 and plated as described in Example 4. To plate the cells, a 0.8 mL suspension of cells ($2 \times 10^6$ cells/mL) in RPMI 1640 culture medium containing 10% FBS and 1% pen/strep mixture was injected into four dendritic cell differentiation cassettes and allowed to incubate at 37° C. After 1 hour to allow for monocyte adhesion, the cassettes were flushed with fresh medium at a flow rate of 400 µL/min, after which flow was set to 10 µL/min. Individual cassettes were removed from the system on days 1, 3, 5, and 7 for analysis using the LIVE/DEAD assay. To label for imaging, the growth medium was removed from the cassette, and a PBS solution containing 20 µL of a calcein-AM solution (50 µM in DMSO) and 20 µL of an ethidium bromide solution (2 mM in DMSO/water, 1:4) was injected. The staining solution was allowed to incubate for 15 min at room temperature, and then the cassette was rinsed with fresh PBS. Imaging was performed using a Nikon microscope with a 20× objective and an integration time of 0.5 s. Cell fluorescence was analyzed by thresholding particles at 20% of the maximum signal and counting using the particle count tool of ImageJ.

Figure 4:
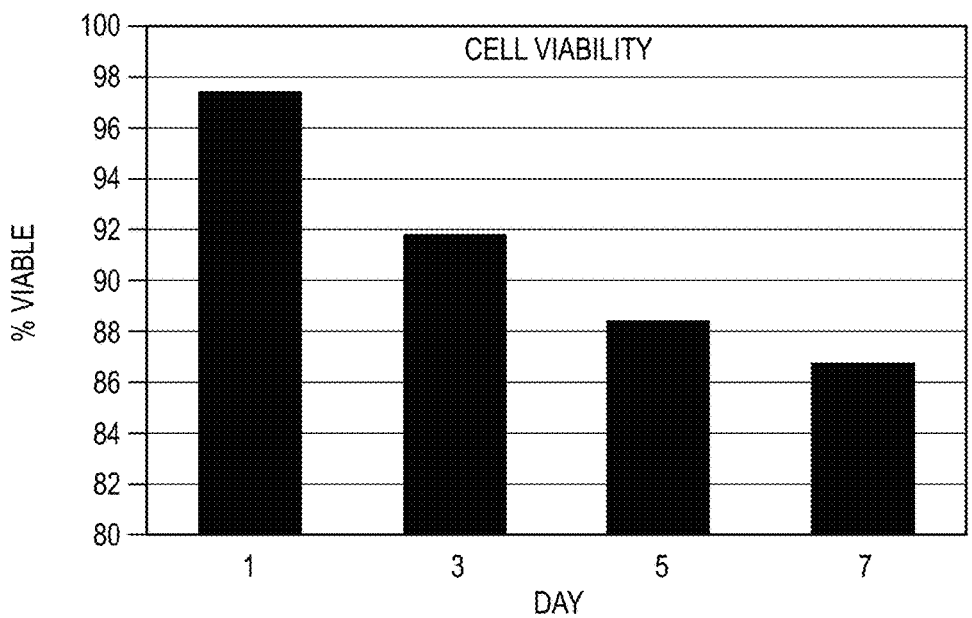
FIG. 4 shows a graph of the results of a cell viability assay carried out on cells perfused for up to seven days using a dendritic cell generation system of the invention.

Cell viability was maintained at over 86% throughout a 7-day period, as represented in FIG. 4 (note that the scale bar on the left starts at 80%). This indicated that most monocytes are able to survive long enough for a DC generation process that lasts up to seven days.

Example 6. Differentiation and Maturation of Dendritic Cells

In order to stimulate bound monocytes to differentiate into dendritic cells, the bound monocytes were subjected to continual perfusion over five days with conversion medium containing IL4 and GM-CSF. The conversion medium was prepared by mixing RPMI-1640 with IL4 to give a final concentration of 500 U/mL and GM-CSF to give 800 U/mL, and a final volume of 20 mL. The differentiation process resulted in detachment of dendritic cells from the polystyrene surface and their retention in the culture chamber, due to the slow flow rate, which was maintained at 10 µL/min. The differentiated, detached dendritic cells were matured by incubation in maturation medium containing IL 1β (2 ng/mL), IL6 (1000 U/mL), TNFα (10 ng/mL), and PGE2 (1 µg/mL) for an additional one day. Switching from one medium to another was performed by manually switching the inlet tubing from one medium reservoir bottle to another. Matured cells were recovered after the six day culture protocol and were characterized by flow cytometry. Matured dendritic cells had a characteristic large and granular phenotype, and had the surface marker profile Lin1 negative, HLA-DR positive, and CD80 positive.

For flow cytometry, cells were first suspended in cold (4° C.) staining buffer (BD 554657) at a concentration between $1 \times 10^7$ and $2 \times 10^7$ cells/mL. A 50 µL aliquot of the cell suspension ($5 \times 10^5$ to $1 \times 10^6$ cells) was placed into a 1.5 mL centrifuge tube. The desired antibody-dye solution was added to the cell suspension at the manufacturer's recommended concentration. For these experiments HLA-DR antibody conjugated with phycoerythrin (R&D Systems FAB4869P) and a lineage cocktail (Lin-1) consisting of different antibodies conjugated to fluorescein (BD 340546) were utilized. This cocktail was formulated to mark several types of white blood cells but not dendritic cells. HLA-DR is a marker of immature dendritic cells and other white blood cells such as macrophages and B-cells, while the lineage cocktail contains markers for different types of white blood cells including CD14+ monocytes but not dendritic cells. These labels served as an indicator that monocytes had been converted into immature dendritic cells. After adding the antibody conjugates to the cell solution, the solutions are mixed by gentle pipette titration and placed in a dark refrigerator at 4° C. for 1 hr. After the incubation, 1 mL of cold staining buffer was added to the centrifuge tube, and the cells were centrifuged at 300×g for 5 min at 4° C. to pellet the cells. After removing the supernatant, the labeled cells were resuspended in 0.25 mL of fresh staining buffer and stored in the dark at 4° C. until analyzed. If analysis was to be done more than 24 hrs later, the cells were fixed with 4% paraformaldehyde and stored at 4° C.

Figure 5A:
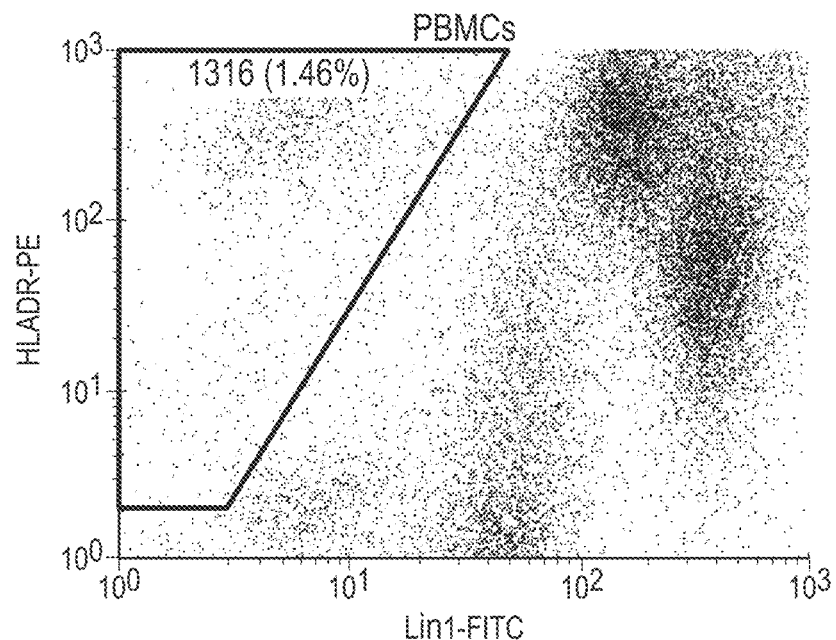
FIGS. 5A and 5B show the results of an experiment to characterize the phenotype of PBMCs prior to use of the dendritic cell generator (FIG. 5A) and DCs obtained after differentiation and maturation in the dendritic cell generator (FIG. 5B).
Figure 5B:
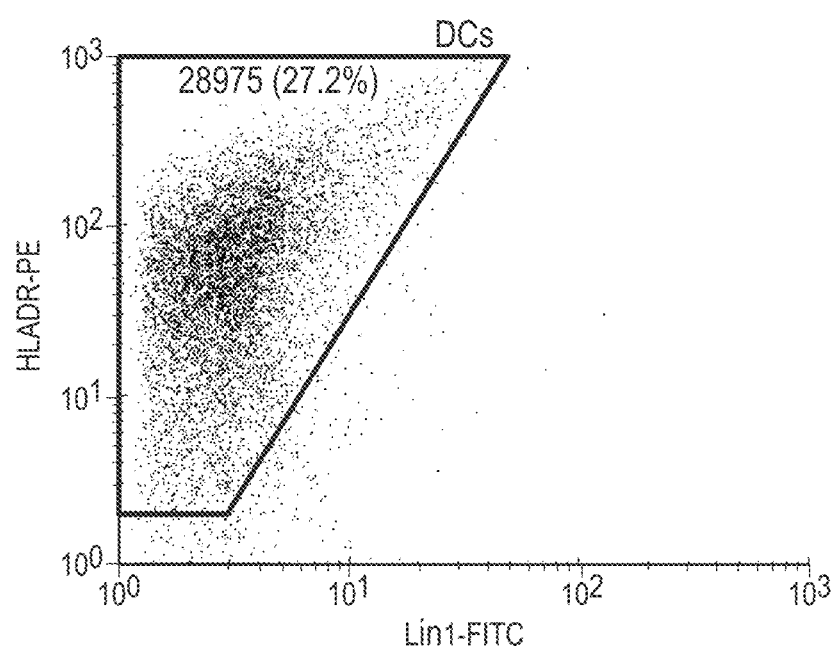

Prior to carrying out flow cytometry, background fluorescence levels and desired electronic volume range were set using an unlabeled sample. Flow cytometry results are shown in FIGS. 5A-5B. FIG. 5A shows results obtained for PBMCs used for initial seeding of the dendritic cell generator system. FIG. 5B shows results obtained for the generated dendritic cells. In the PBMCs, several different populations of cells can be seen, which is indicative of the expected mixture of several different types of cells that were stained by both Lin-1 and HLA-DR antibodies. A sparse population of cells can be seen in the left side of FIG. 5A, which is where DCs are expected due to low Lin-1 expression and high HLA-DR expression. Only 1.46% of cells analyzed were found in this region. After DC generation, this region became much more heavily populated, with 27.2% of cells showing characteristics of DC.

Example 7. Prototype of Microfluidic Dendritic Cell Generator

Figure 6A:
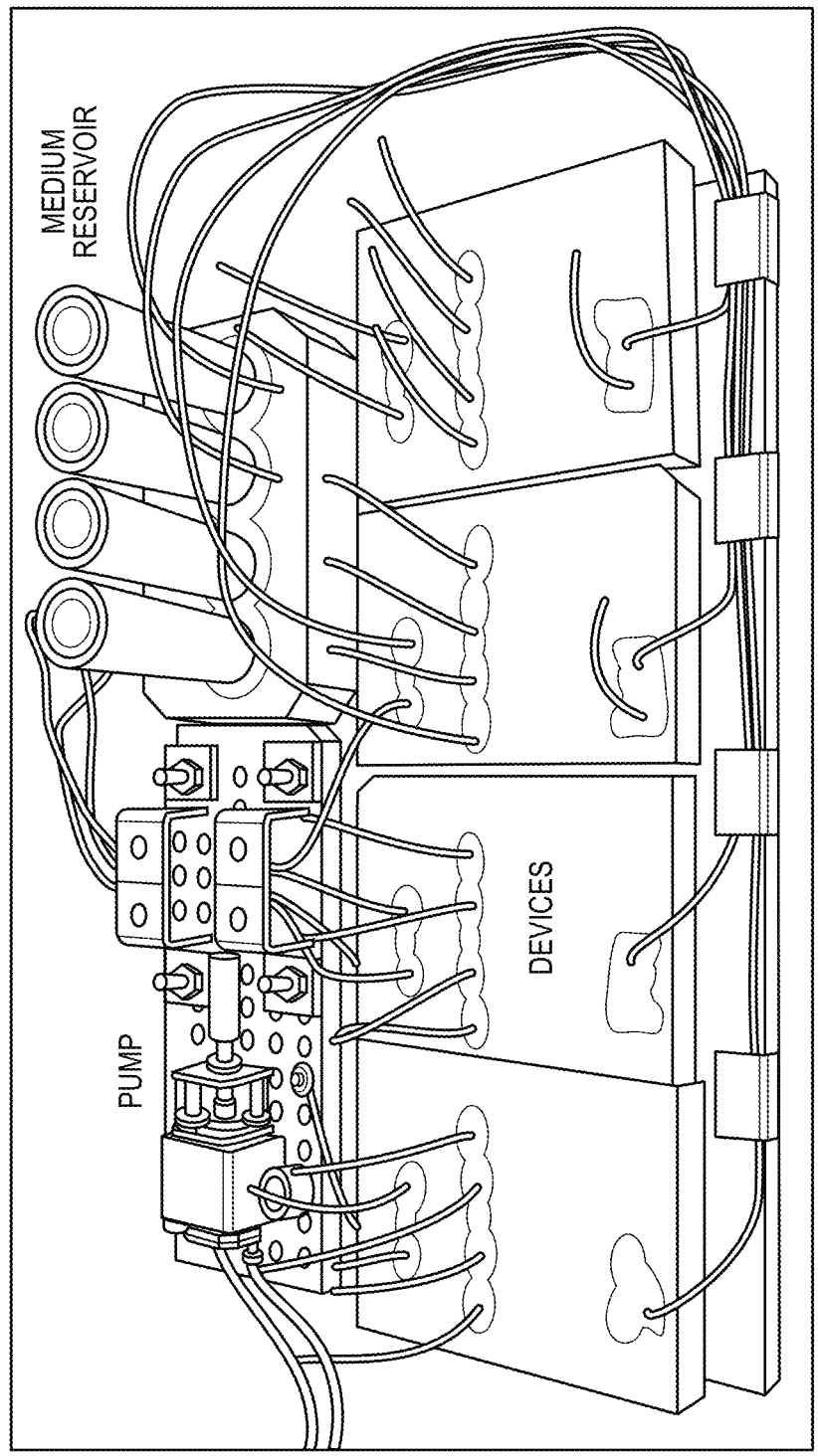
FIGS. 6A-6D show system setup and characterization where (A) shows an image of the chip-based cell culture platform. (B(i)) shows a cross-sectional view of the circular-cross section micro-channels. Scale bar, 300 μm. (B(ii)) shows a magnified view of the tubing coil within the PDMS block. (B(iii)) Schematic diagram illustrating the turning of the pump shaft as it locally compresses the tubing and drives fluid flow. (B(iv)) shows a schematic diagram of the fluidic channels which are grouped as four channels with four such groups connecting to a single bubble trap. The chip shown in (A) contains a total of sixteen such groups connected to four bubble traps. (C(i)) shows the flow rate measurement of the four independent flow circuits through the four fluidic devices, n=3. (C(ii)) shows the flow rate measurement of the miniaturized pump determined via particle image velocimetry (PIV) in both forward and reversed flow direction. (C(iii)) shows pump stability under various pressures, n=3. (C(iv)) shows the stability of the pump over a 4 day period, n=3. (D) Shows schematic layout of the device operation for cell injection, cell culturing, and perfusion assay.
Figure 6B:
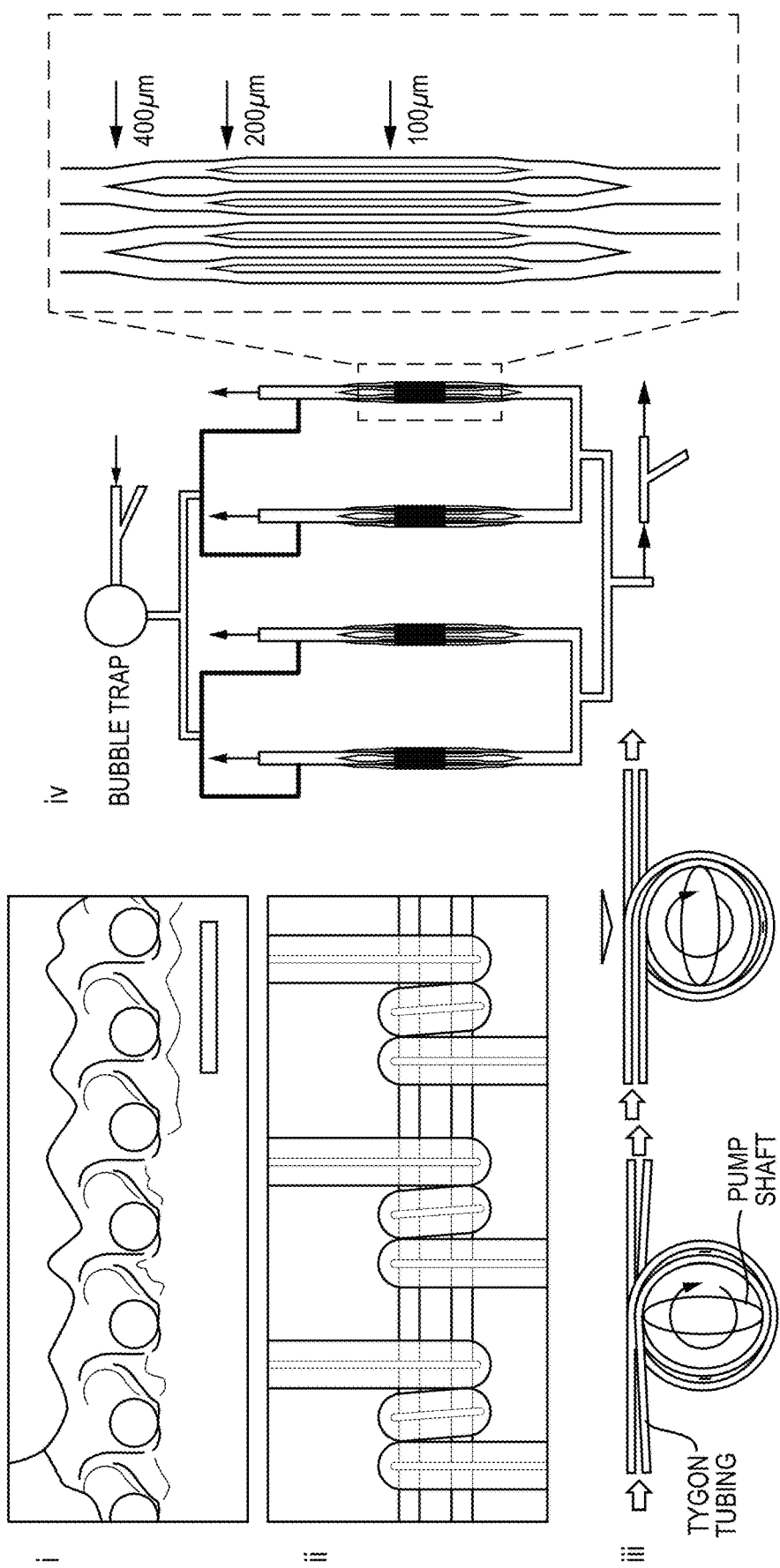
Figure 6C:
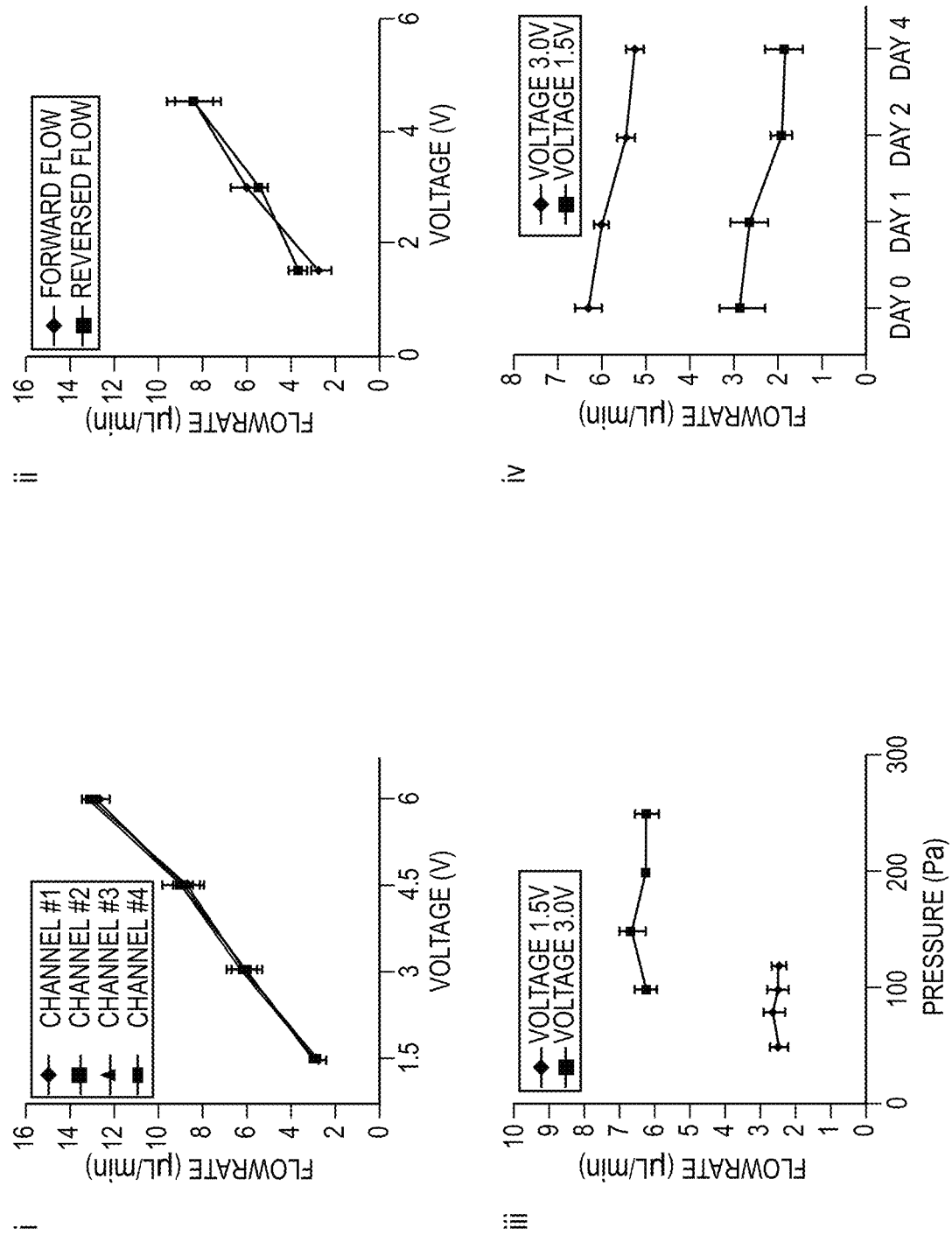
Figure 6D:
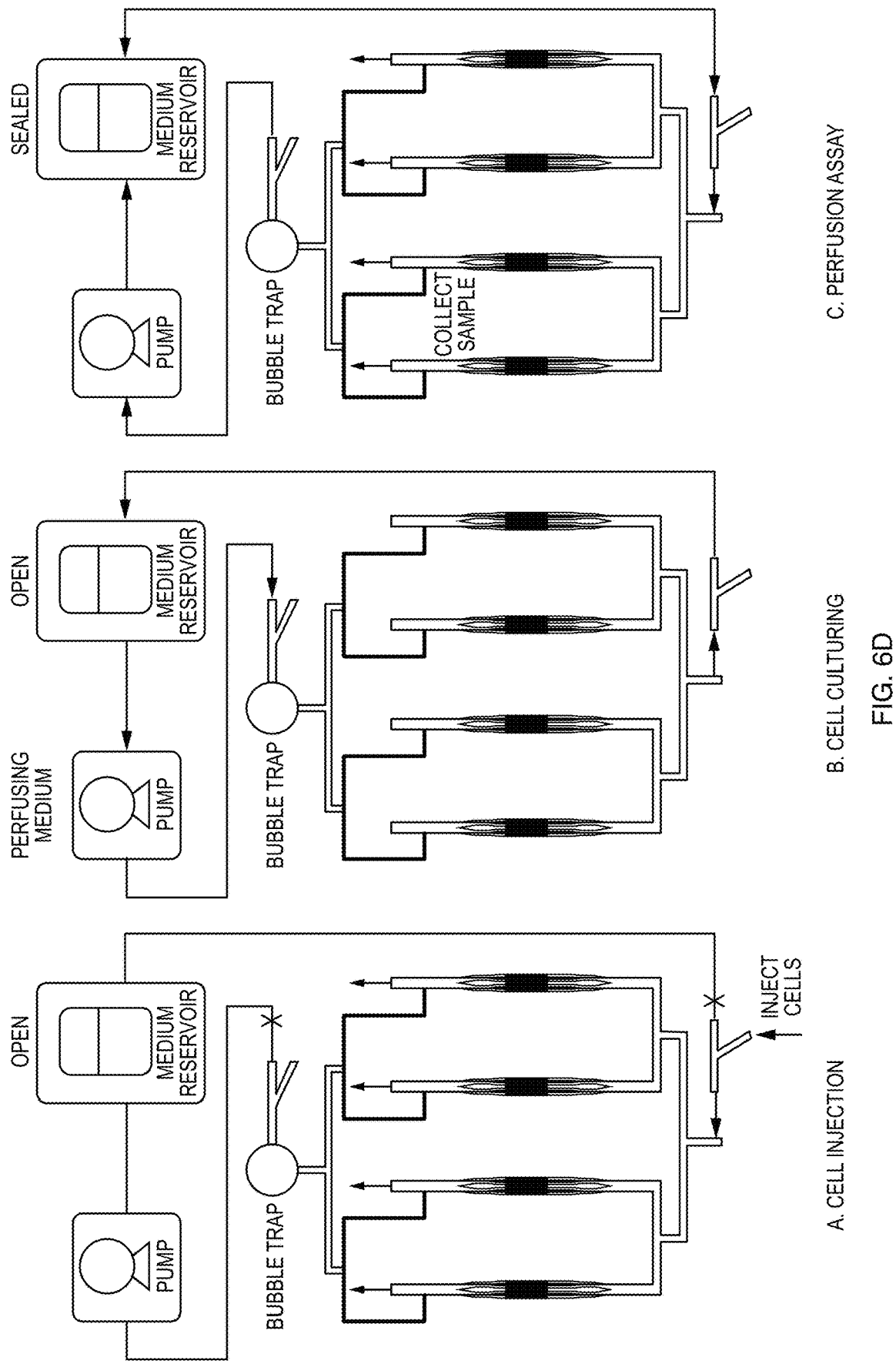

A standalone fluidic cell culture and perfusion platform for recapitulation of microvasculature is shown in FIG. 6A. As shown in FIG. 6B, four branching channel networks, connected in parallel, are coupled to a custom-designed, on-chip peristaltic pump. The pumping mechanism, comprised of a small motor and a rotating elliptical shaft, is capable of providing continuous and consistent flow of culture medium to the channel network. The flow rate can be controlled by adjusting the rotational speed of the metal shaft via changes in applied voltage (0-6 V corresponding to approximately 0-16 µL/min) as shown in FIG. 6C. FIG. 6C also shows that each of the four channels has the same flow rates in both forward and reverse direction, and the pump has little loss of stability over the 4-day time scale studied, a time scale similar to that required for the cell culture system. A bubble trap (FIG. 6B, D) was incorporated into this system to eliminate disruption of the cell culturing and subsequent mechanical detachment of the cell monolayers by air bubbles. Additionally, the pumping platform allows for direct injection of cells with the pumping mechanism turned off, which enables injection and loading of cells either via manual injection or at higher flow rates using an external pump.

This standalone fluidic cell culture and perfusion platform operates without using a filter. By maintaining the fluid flow rate below the sedimentation rate, dendritic cells remain within the culture chamber because of their mass. In other words, dendritic cells will sink towards the bottom of the cell culture chamber and therefore remain in the cell culture chamber without requiring a filter. This simplifies the overall design of the system and improves, for example, the required maintenance of the system. A filterless system will not suffer clogged filters or require that a filter be replaced for example. A flow rate that is lower than the sedimentation rate can be calculated according to Equation 1, $$v_{max} = \frac{(\psi d_p)^2}{150\mu} g(\rho_{cell} - \rho_{liquid}) \frac{\epsilon^3}{1-\epsilon} \quad \text{Equation 1}$$

where $v_{max}$ is the liquid velocity beyond which cells will be lifted upwards, $\psi$ is shape factor of cells (ratio of surface area of the cells to surface area of a sphere of equal volume; note that cells are not perfectly spherical and this factor is expected to be below 1), $d_p$ is a diameter of a spherical particle of volume equal to that of a cell, $\mu$ is viscosity of liquid containing cells, g is the gravitational constant $\rho_{cell}$ is the density of cells, $\rho_{liquid}$ is a density of liquid containing cells, and $\epsilon$ is a fraction of the volume of interest that is not occupied by cells.

Figure 7A:
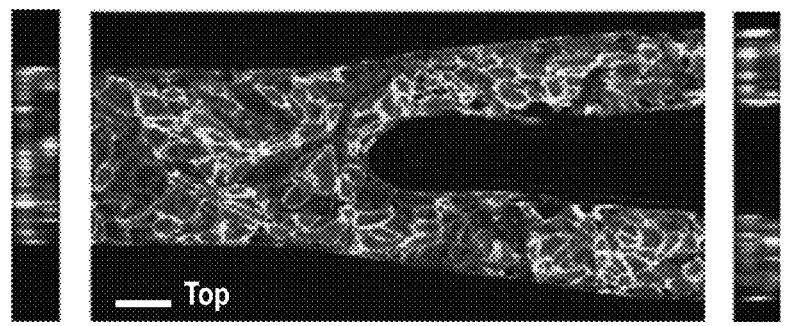
FIGS. 7A-7C show HUVEC cells cultured on a chip that are viable and functional within 2 days. Immuno-fluorescence staining of the micro-vessel network shown as top view (middle) and cross-sectional view of the circular channels (sides) in the micro-vessel network at (A) 400 μm segment, (B) 200 μm segment, (C) 100 μm segment. Scale bar, 100 μm; CD31-green, DAPI-blue. White arrows indicate void space between cells. Red arrows indicate the cross section of the 100 μm micro-vessels.
Figure 7B:
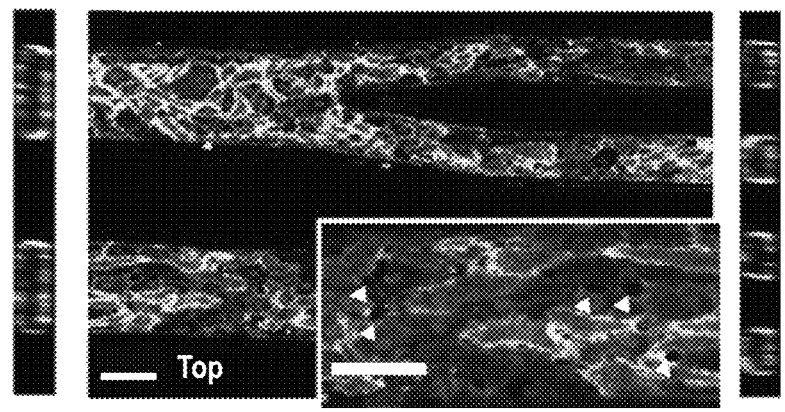
Figure 7C:
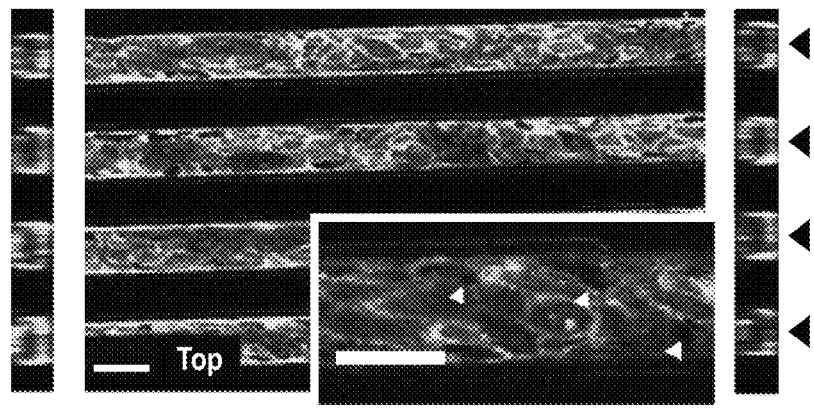

Within this device, HUVECs were able to attach, proliferate, and cover the entire luminal surface with pre-defined branching vessel structures within 2 days (FIG. 7). This result also confirms that viability was not comprised by the micropump or any other aspect of the chip-based culture system. Expression of CD31 and VE-cadherin at the cell-cell interface outlined the endothelial morphology, confirming the formation of inter-cellular junctions. Cells aligned along the micro-channels is consistent with the morphology of endothelial cells in vivo which elongate and align in the direction of blood flow. The perfusion culture on chip resulted in a higher nitric oxide release upon introduction of acetylcholine, atorvastatin, and sildenafil compared to a well-plate static culture, demonstrating the benefit of recapitulating physiological conditions in terms of 3-dimensional geometry and fluid flow characteristics.

This system occupies a footprint of approximately 10 cm×5 cm and can be easily placed in a standard incubator for cell culturing at physiological conditions. The system can also be placed under a microscope for imaging while providing constant flow through the channels. While an external power source is needed, such sources are relatively small, and a single source can be utilized to power multiple chips. In this work, the reservoirs all contained the same culture medium, but this system can be easily configured to add reservoirs for multiple types of media.

To stimulate bound monocytes to differentiate into dendritic cells, the bound monocytes were subjected to continual perfusion over five days with conversion medium containing IL4 and GM-CSF. The conversion medium was prepared by mixing RPMI-1640 with IL4 to give a final concentration of 500 U/mL and GM-CSF to give 800 U/mL, and a final volume of 20 mL. The differentiation process resulted in detachment of dendritic cells from the polystyrene surface and their retention in the culture chamber, due to the slow flow rate, which was maintained at 2 µL/min. The differentiated, detached dendritic cells were matured by incubation in maturation medium containing IL 1β (2 ng/mL), IL6 (1000 U/mL), TNFα (10 ng/mL), and PGE2 (1 µg/mL) for an additional one day. Switching from one medium to another was performed by manually switching the inlet tubing from one medium reservoir bottle to another. Matured cells were recovered after the six-day culture protocol and were characterized by flow cytometry. Matured dendritic cells had a characteristic large and granular phenotype, and had the surface marker profile Lin1 negative, HLA-DR positive, and CD80 positive.

Figure 8:
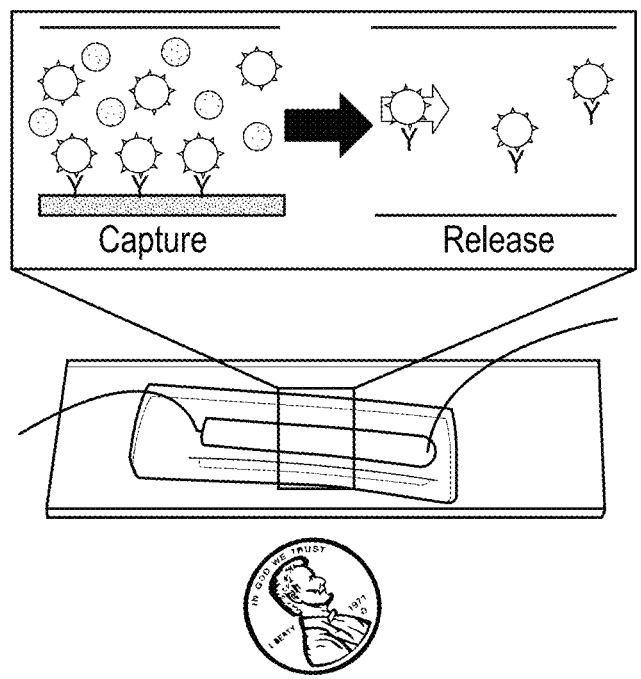
FIG. 8 shows exemplary microfluidic devices coated with degradable hydrogels containing antibodies for selective capture of target cells from whole blood and non-destructive release under mild conditions.
Figure 9A:
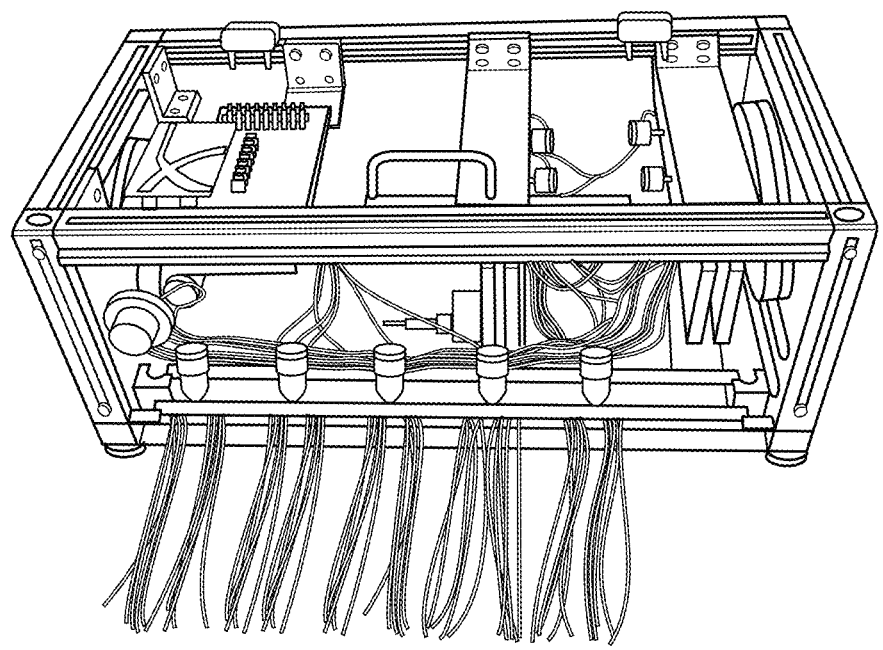
FIGS. 9A-9E show an automated fluid injector system pumping pump 6 different kinds of aqueous solutions into 48 fluidic devices. An additional pressure-based pumping system was included to pump viscous hydrogel solutions into the devices. (A) photograph of the automated system that would typically be connected to a gas cylinder and laptop. (B) fluid reservoirs. (C) the white tubing is seen in (A) connected to individual fluidic chips. (D) system diagram showing channel and pumping layouts. (E) an image of a home-built LabView program that allowed specification of incubation times for each fluid type along with flow rates for the aqueous pumping system and the hydrogel pumping system.
Figure 9B:
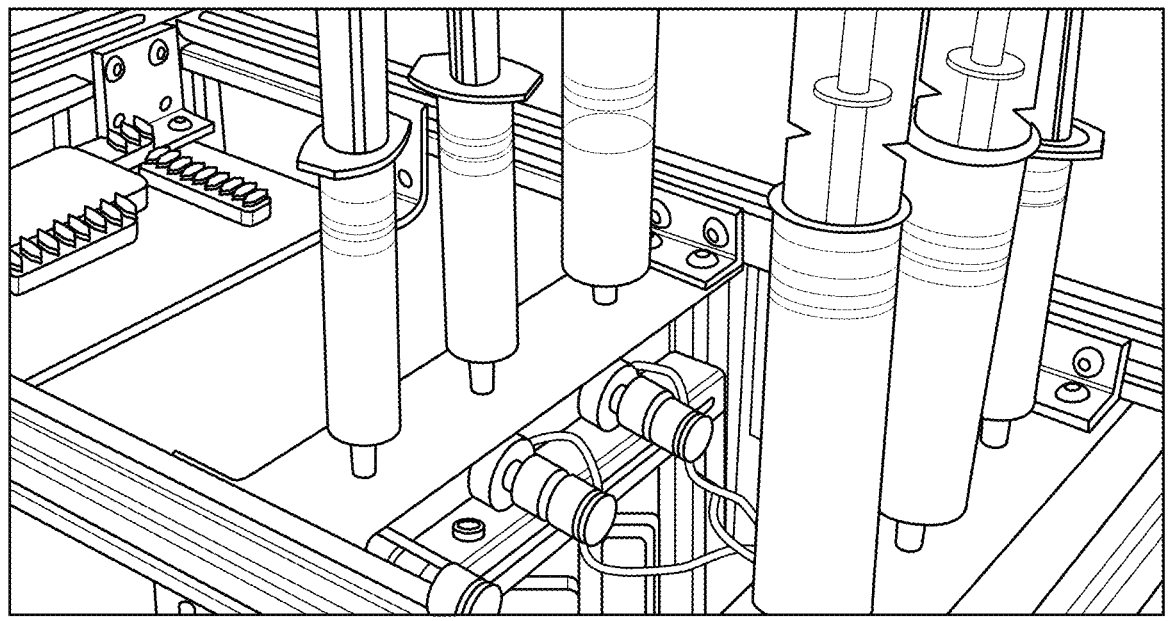
Figure 9C:
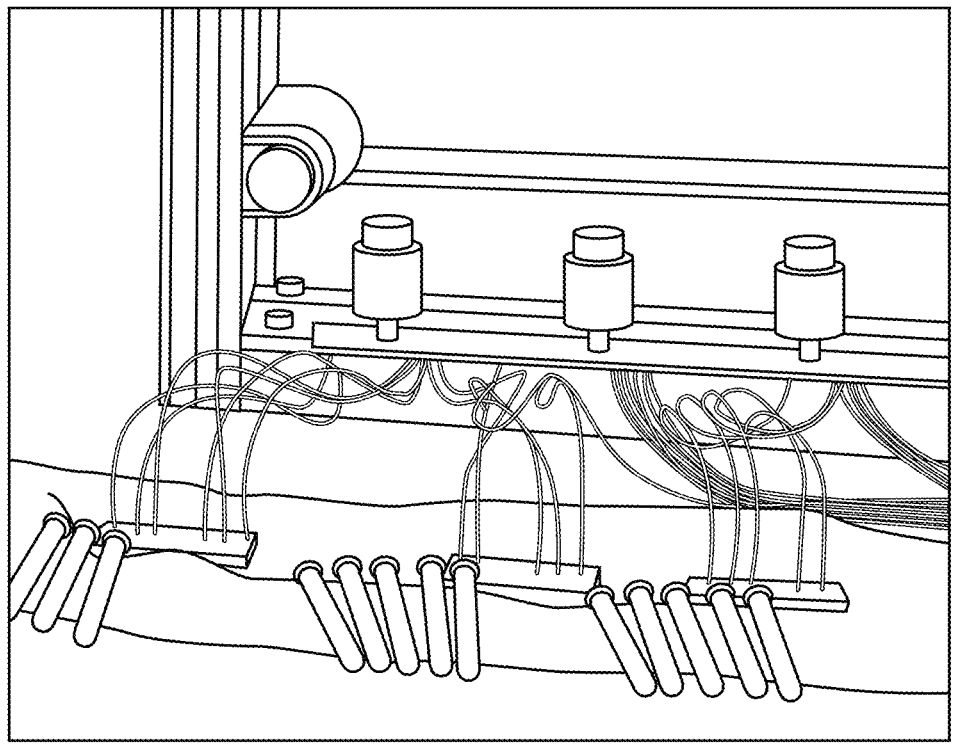
Figure 9D:
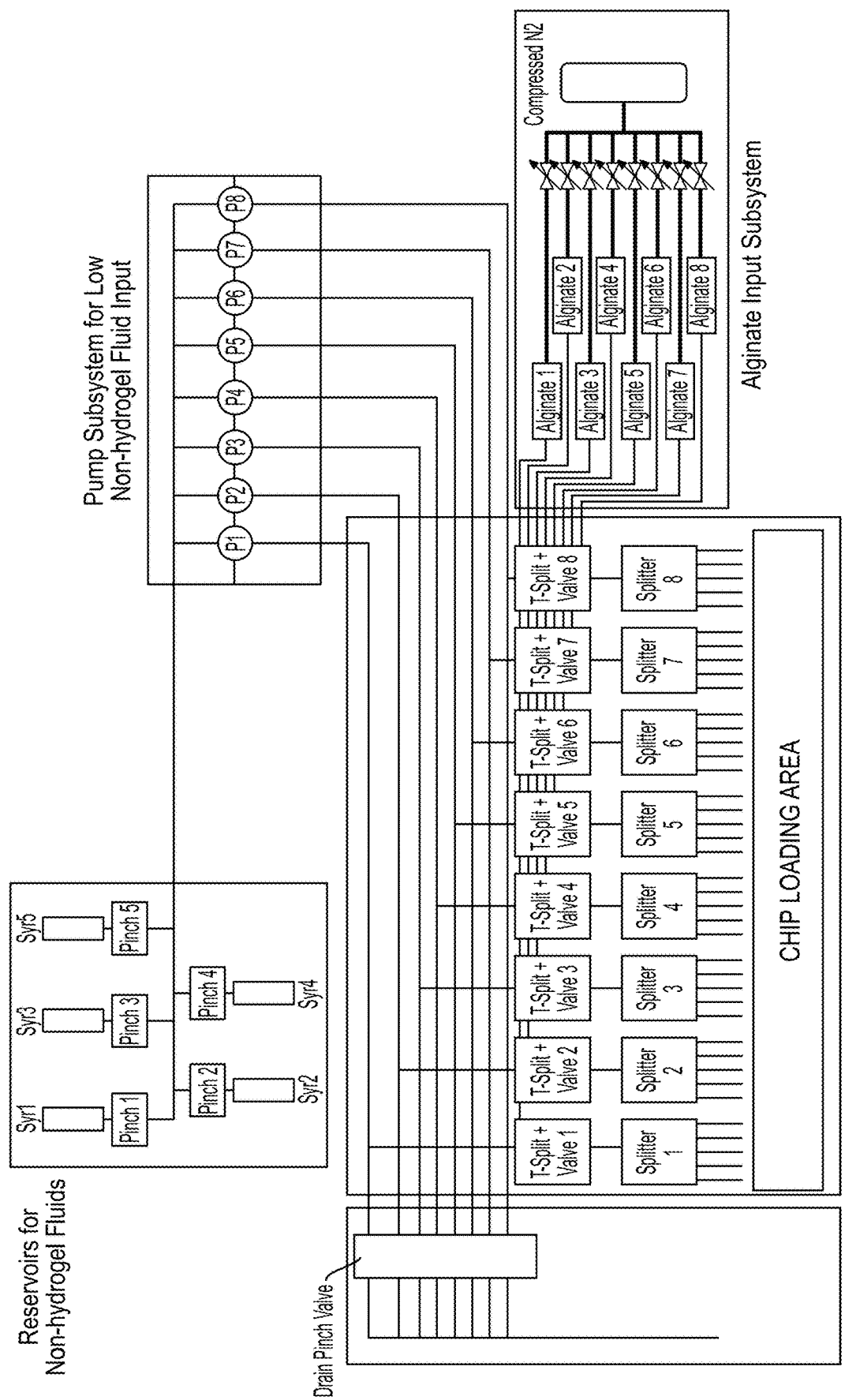
Figure 9E:
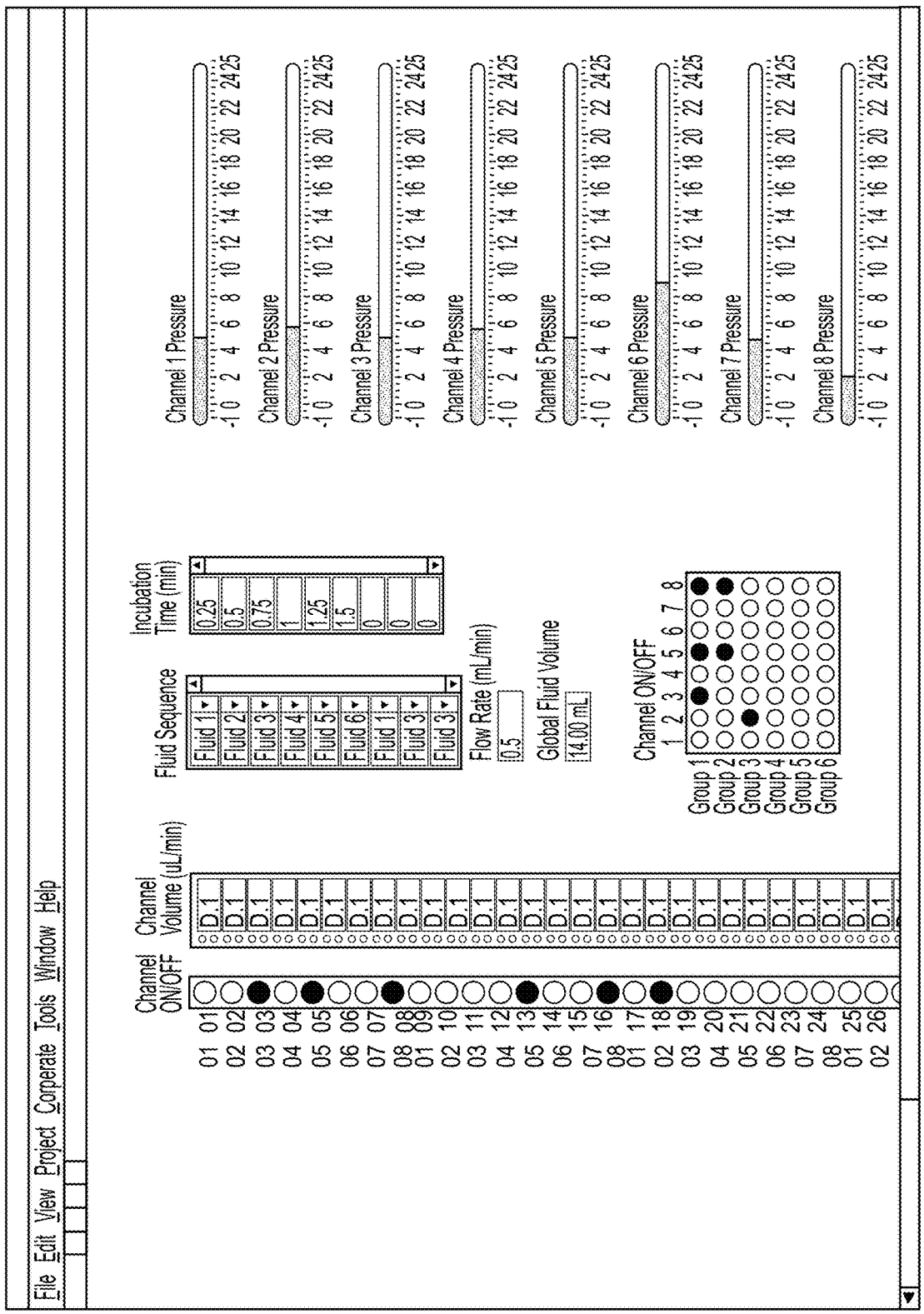

Example 8. Affinity-Based Purification of Target Cell Populations from Whole Human Blood The coating is designed to combine antibody-mediated immunospecific capture with the non-specific adhesion affinity-based methods for microfluidic purification of multiple cell types from blood for over a decade. A significant contribution to this area was the design of surface coatings made of a copolymer of alginate and poly(ethylene glycol) (PEG) functionalized with capture antibodies as described in, for example, Hatch A, Hansmann G, Murthy S K. Engineered Alginate Hydrogels for Effective Microfluidic Capture and Release of Endothelial Progenitor Cells from Whole Blood. Langmuir. 2011; 27: 4257-4264 and Hatch A, Pesko D M, Murthy S K. Tag-Free Microfluidic Separation of Cells against Multiple Markers. Anal. Chem. 2012; 84: 4618-4621. This coating was designed to combine antibody-mediated immunospecific capture with the non-specific adhesion properties of PEG and the degradable nature of alginate. Native alginate solutions are free flowing liquids which form hydrogels in the presence of divalent cations (like calcium). These hydrogels have a consistency similar to Jell-O but thin layers of these hydrogels can be fully dissolved by bringing in contact with a chelator such as ethylene diamine tetraacetic acid (EDTA). This 'on-demand' dissolution capability is retained in the coatings which can capture cells expressing target antigens within microfluidic devices as shown in FIG. 8. These devices have hexagonal arrays of 100 μm vertical pillar structures to increase surface area for cell capture, as illustrated in FIG. 6b. Following the capture phase, the isolated cells can be eluted out of the chip by flowing in a solution of EDTA. As described below, this coating will be incorporated into the culture chip shown above to add the capability to capture CD14+ monocytes from whole blood The design and fabrication of the system uses building blocks described above in four major steps: incorporation of pillar array structures within the linear microchannels of the culture system prototype shown in FIG. 6 to increase surface area for efficient capture of monocytes from blood; modifying the placement of fluid reservoirs to allow placement of four unique fluid source vials and one large waste vial; (ii) coating of microchannels with 'capture-release' coating functionalized with antibodies against CD14 and initial testing with commercially available purified CD14+ human peripheral blood monocytes; and (iv) testing with whole human blood to ensure that 'capture-release' coating can capture CD14+ monocytes with high purity; and testing of perfusion with culture medium.

A computational technique to identify pillar array parameters (pillar diameter, offset, and length) as described in prior publications (e.g., Zhu B, Smith J, Yarmush M L, Nahmias Y, Kirby B J, Murthy S K. Microfluidic enrichment of mouse epidermal stem cells and validation of stem cell proliferation in vitro. Tissue Eng Part C Methods. 2013; 19: 765-773 and Green J V, Radisic M, Murthy S K. Deterministic lateral displacement as a means to enrich large cells for tissue engineering. Anal. Chem. 2009; 81: 9178-9182). Briefly, a coupled computational fluid dynamics (CFD) particle advection code will be utilized to track a uniform distribution of cells through the microchannel. A range of offsets from 0 (straight array) to 75 mm (hexagonal array) will be examined. Given the size of monocytes ~10 mm in diameter and taking into account the size range of non-target cells in the blood (2-10 mm, including disc-shaped erythrocytes), as described in, for example, Sethu P, Sin A, Toner M. Microfluidic diffusive filter for apheresis (leukapheresis). Lab Chip. 2006; 6: 83-89, an offset can be optimized to ensure that cells larger than 8 mm collide with at least 70% of the pillars. These arrays are created in rectangular cross-section PDMS microchannels via standard soft lithography. Microchannels with 400 mm widths with 10-20 mm diameter pillars are the starting point. While a branch channel is shown in FIG. 6, it is not required.

As shown in FIG. 6A, the media reservoir tubes are seated in a custom-designed PDMS block. A similar block will be created to house four 2 mL vials for reagents and a larger 5 mL tube for waste. An additional slot will be created for a product vial. Note that this preparation is for device operation in a 'semi-manual' mode where source and exit tubes will be moved manually between reservoir tubes and waste/product tubes.

PEG-alginate hydrogel coatings will be prepared as described previously in, for example, Hatch A, Hansmann G, Murthy S K. Engineered Alginate Hydrogels for Effective Microfluidic Capture and Release of Endothelial Progenitor Cells from Whole Blood. Langmuir. 2011; 27: 4257-4264, applied onto the surfaces of the pillar-array microchannels with a surface coating of anti-CD14 capture antibody (Abcam). Performance testing of the pillar array includes the capture of commercially available purified CD14+ human peripheral blood monocytes (Lonza). Cells will be flowed into the channels at flow rates corresponding to wall shear levels of 0.3-0.5 dyn/cm$^2$, which is an optimal range for CD14+ cell capture identified by Cheng and coworkers (See, for example, Cheng X H, Gupta A, Chen C C, Tompkins R G, Rodriguez W, Toner M. Enhancing the performance of a point-of-care CD4+T-cell counting microchip through monocyte depletion for HIV/AIDS diagnostics. Lab Chip. 2009; 9: 1357-1364). Following capture and a wash with PBS, cells are eluted out using a solution of 50 mM EDTA in PBS and counted using a Beckman Coulter Quanta SC benchtop flow cytometer. The design can be further optimized until the capture level of monocytes is maximized. For a typical transcriptomics experiment with CD4+ T cells, for example, ~3×10$^5$ DCs which are generated by a comparable number of monocytes. The size and total area of microchannels and pillar arrays can be tailored to achieve this level of total monocytes capture in a chip having four separate capture compartments with the footprint of that shown in FIG. 6A.

The efficacy of monocyte capture will be characterized by measuring the composition (% purity) of CD14+ cells captured within the microchannels and the capture efficiency (number of CD14+ cells recovered following purification divided by the number of CD14+ cells in whole blood injected into the device) via flow cytometry. A range of flow rates between 5-15 mL/min will be examined using the custom-designed integrated pump to maximize both purity and efficiency, with greater emphasis on the former. A minimum purity level of 95% is identified as a milestone for characterization.

The monocytes adhered within the culture chips are perfused with culture medium containing no cytokines over a period of 6-8 days to verify the ability of the chip to maintain cells in a viable state. All coating materials and device components are sterilized by autoclaving. For culture medium (RPMI 1640) perfusion, flow rates in the range of 5-15 mL/min are tested with the objective of determining if any cell detachment occurs at the higher flow rate range. The cells captured within the microchannel will deposit extracellular matrix proteins and become strongly adhered 12-24 hours after capture, and that viability is retained for the full 6-8 day period to be examined. A milestone of <10% cell loss via detachment and viability on chip at 100% represents successful monocyte adherence.

Automation and flow control capability will be designed at the level of an individual chip of the size shown in FIG. 6A. A key strength of this chip design is the highly compact size of the pump. In contrast to the comparatively large system shown in FIG. 9, automation at the single chip level will be enabled by the use of small components that can be assembled on a compact breadboard. Such small-scale automation is highly desirable in an application such as monocyte-to-DC conversion because this will allow individual chips to be matched with individual patients and for any given number of patients only that number of chips and no more will need to be used, thereby ensuring efficient operation. In addition, such automation also allows for efficient space utilization within incubators.

Figure 10:
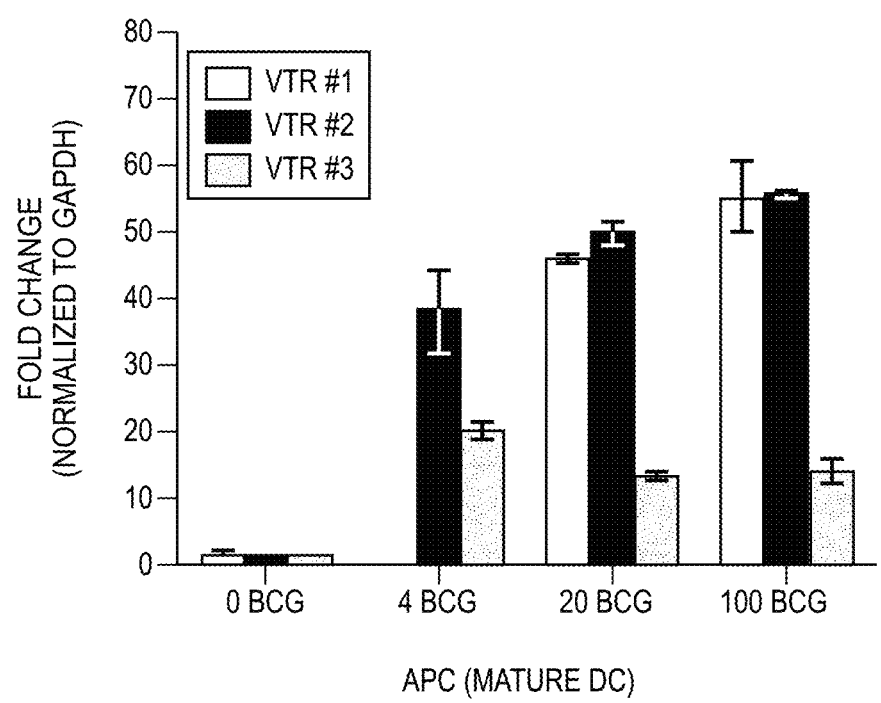
FIG. 10 shows BCG-induced increases in IL2 mRNA at the 24 hour time point measured via RT-PCR following stimulation of memory CD4+ T cells with BCG-infected DCs (20:1 ratio) from three PPD+ individuals.

FIGS. 11A-11D show the result of an experiment where memory CD4+ T cells were purified from three PPD+ individuals with Miltenyi negative selection immunomagnetic purification kits resulting in >97% pure memory CD4+ T cells. These cells were stimulated with autologous DCs generated using the conventional culture method (20:1 ratio in the culture of T cells to DCs) that were uninfected or infected with a BCG MOI of 4, 20, or 100. Total RNA was harvested at 24, 48, and 72 hours. qRT-PCR for IL2 mRNA was performed to determine what conditions provide the best ability to see BCG-induced changes. FIG. 10 represents a relatively simple way to compare DCs generated conventionally vs. the microDEN system.

Figure 11A:
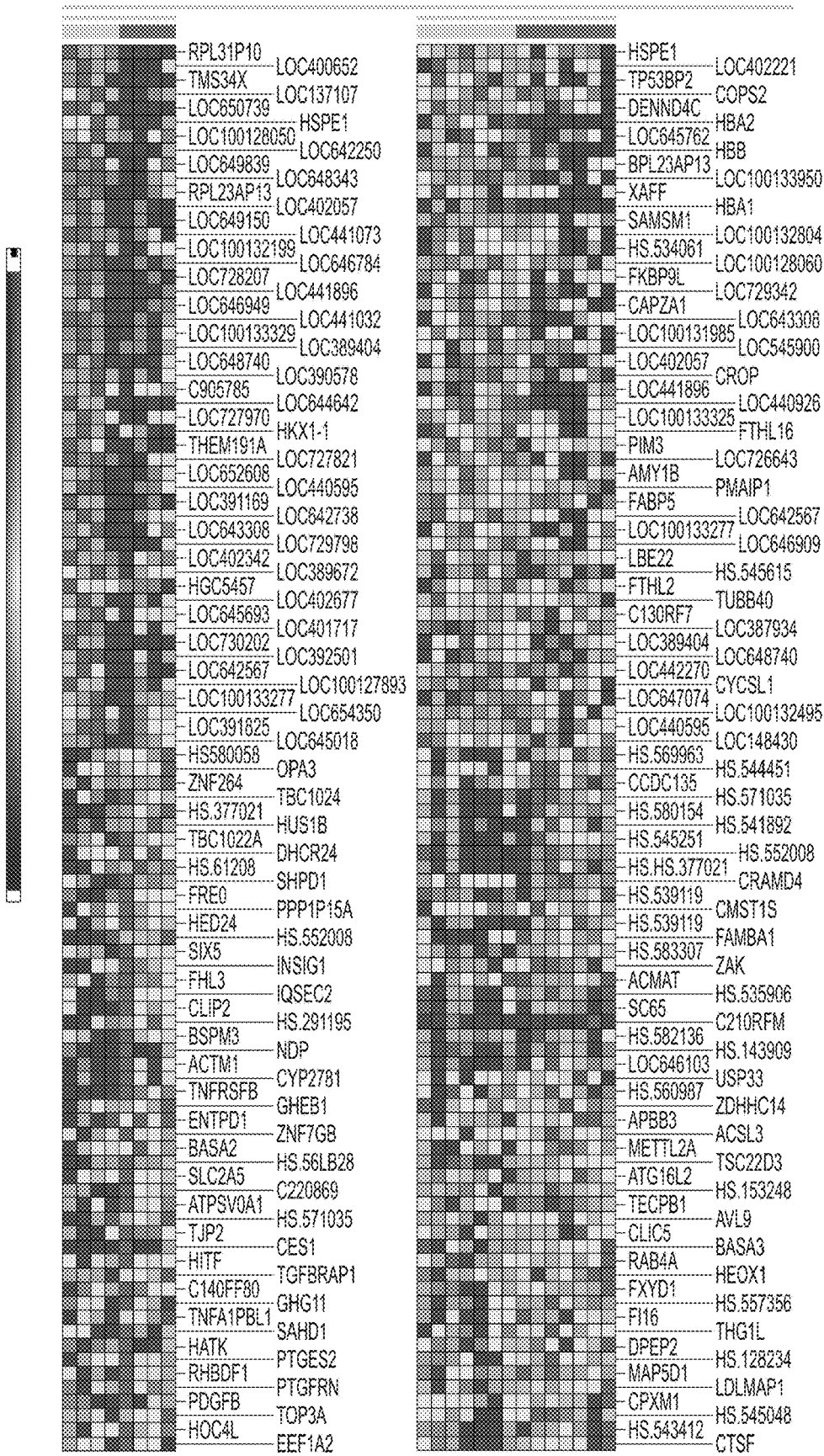
Figure 11B:
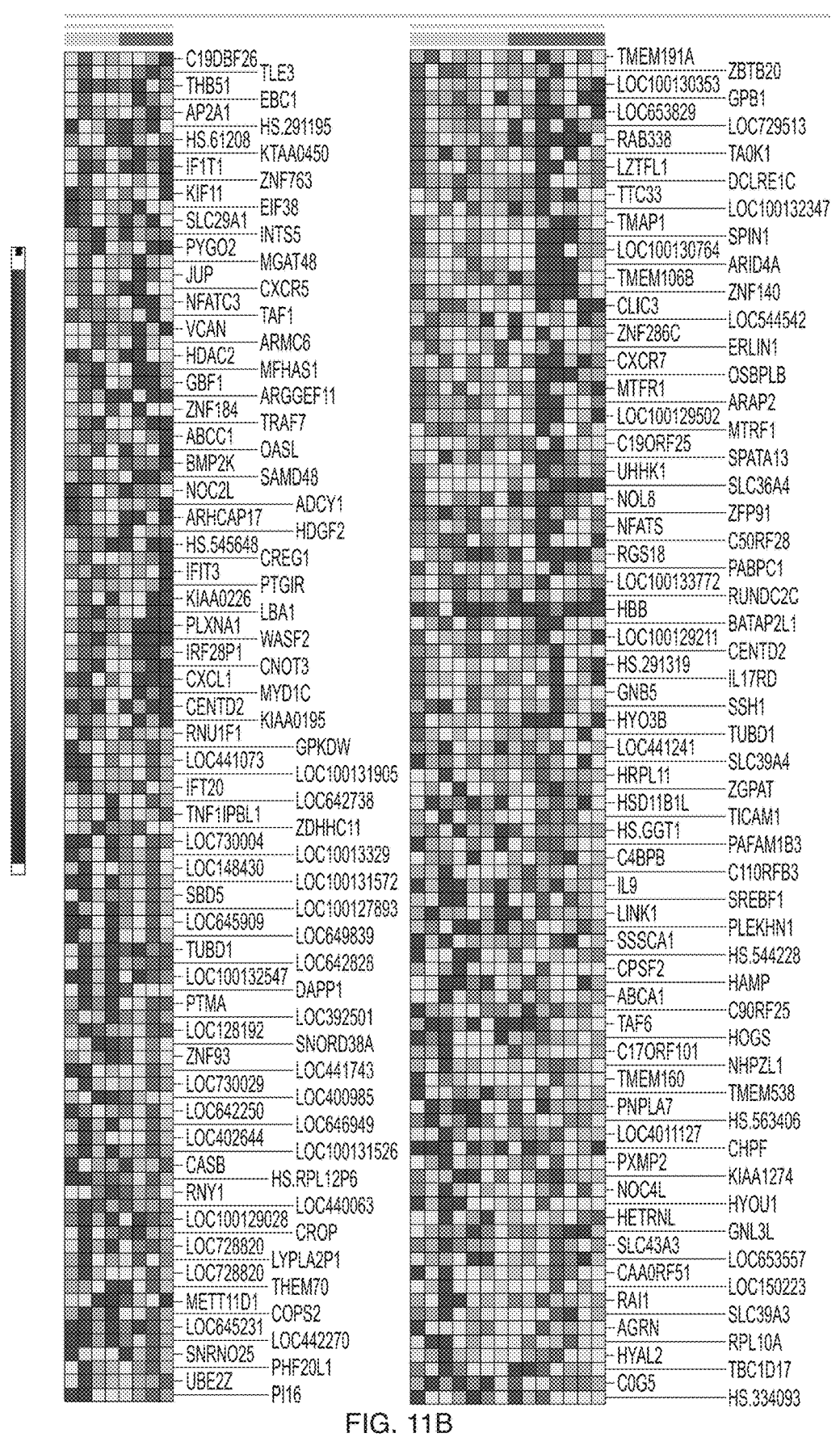
Figure 11C:
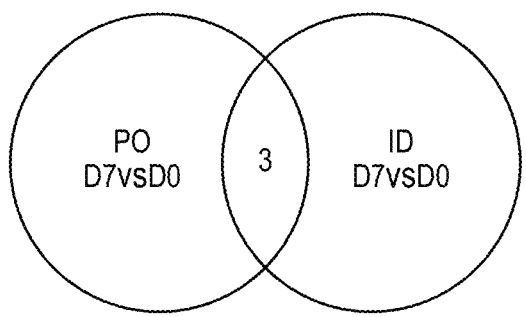
Figure 11D:
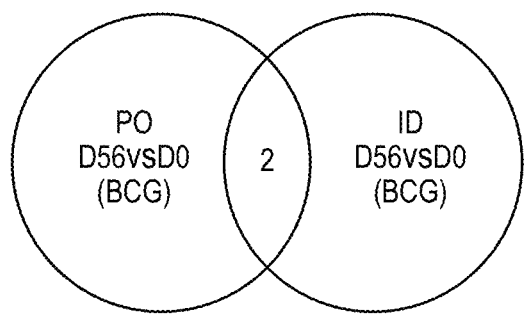

An experiment was also performed microarray experiments to study the molecular transcriptomes of memory CD4+ T cells induced by oral (PO) and intradermal (ID) BCG in an NIAID VTEU-sponsored trial DMID-01-351. The preliminary data (generated by microarrays experiments with 4 PO and 7 ID BCG recipients) indicate that unique CD4+ T cell molecular signatures are induced by PO vs. ID BCG. Illumina Bead Arrays were used for these experiments. Direct ex vivo and BCG re-stimulated transcriptomes pre-vaccination (day 0), at the peak of T cell activation (day 7) and at a later memory/effector time point (day 56). GenePattern Analysis was used to compare pre- and post-vaccination transcriptomes directly ex vivo and after BCG in vitro re-stimulation. FIG. 11A shows heat maps for the top most altered genes directly ex vivo comparing pre-vaccination and day 7 post-vaccination (peak of T cell activation) responses, for PO and ID BCG groups separately. BCG vaccination reproducibly altered expression patterns similarly across individuals within each group. The Venn diagram comparing the unique gene lists identified on day 7 post-vaccination (FIG. 11B), demonstrates that PO and ID BCG induced distinct activation patterns. FIG. 11C shows heat maps for the top most altered genes after BCG re-stimulation comparing pre-vaccination and day 56 post-vaccination (memory/effector responses), for PO and ID BCG groups separately. The Venn diagram comparing the unique gene lists identified on day 56 post-vaccination (FIG. 11D) demonstrates that PO and ID BCG induced distinct memory patterns. Preliminary GSEA analysis indicated that a set of asthma-associated genes were enriched in PO BCG recipients at both day 7 and 56. These results demonstrate the ability to perform genome-wide expression studies, and to analyze the differential gene profiles induced.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

What is claimed is:

1. A dendritic cell generation system comprising:
   one or more dendritic cell differentiation cassettes comprising:
      a plastic body comprising a cell culture chamber, the chamber comprising a monocyte-binding substrate;
      a fluid inlet port; and
      a fluid outlet port;
      wherein the plastic body, the fluid inlet port, and the fluid outlet port are fluidically coupled to the cell culture chamber and configured to provide flow of a liquid culture medium across the substrate from the inlet port to the outlet port;
   a culture medium reservoir fluidically coupled to the fluid inlet port of the one or more dendritic cell differentiation cassettes;
   a fluid collection reservoir fluidically coupled to the fluid outlet port of the one or more dendritic cell differentiation cassettes; and
   a pump configured for pumping fluid from the culture medium reservoir, through the cell culture chamber of the one or more dendritic cell differentiation cassettes, and into the fluid collection reservoir.

2. The dendritic cell generation system of claim 1, wherein the pump mechanism comprises a pump built into each of the one or more dendritic cell differentiation cassettes.

3. The dendritic cell generation system of claim 1, wherein the pump mechanism comprises one or more pumps detached from the one or more dendritic cell differentiation cassettes.

4. The dendritic cell generation system of claim 1 comprising a processor, a memory, and a set of instructions executable by the processor for carrying out a method of preparing dendritic cells of a subject.

5. The dendritic cell generation system of claim 1 that is configured as a single disposable unit.

6. The dendritic cell generation system of claim 1 that is configured for operation within a cell culture incubator.

7. The dendritic cell differentiation cassette of claim 1, wherein the monocyte-binding substrate comprises a polystyrene surface that binds monocytes but not differentiated dendritic cells.

8. The dendritic cell differentiation cassette of claim 1, wherein the monocyte-binding substrate forms a bottom of the cell culture chamber and comprises a flat surface.

9. The dendritic cell differentiation cassette of claim 1, wherein the fluid inlet port and fluid outlet port are disposed at opposite ends of the cell culture chamber.

10. The dendritic cell differentiation cassette of claim 1 that is assembled from a polystyrene bottom slab and a poly(methyl methacrylate) (PMMA) top slab, the top and bottom slabs separated by a PMMA cell culture chamber slab.

11. A method of preparing dendritic cells of a subject, the method comprising the steps of:
   providing a liquid sample comprising monocytes of the subject to a dendritic cell generation system comprising:

one or more dendritic cell differentiation cassette comprising:
   a plastic body comprising a cell culture chamber, the chamber comprising a monocyte-binding substrate;
   a fluid inlet port; and
   a fluid outlet port;
   wherein the plastic body, the fluid inlet port, and the fluid outlet port are fluidically coupled to the cell culture chamber and configured to provide flow of a liquid culture medium across the substrate from the inlet port to the outlet port;
   a culture medium reservoir fluidically coupled to the fluid inlet port of the one or more dendritic cell differentiation cassettes;
   a fluid collection reservoir fluidically coupled to the fluid outlet port of the one or more dendritic cell differentiation cassettes; and
   a pump configured for pumping fluid from the culture medium reservoir, through the cell culture chamber of the one or more dendritic cell differentiation cassettes, and into the fluid collection reservoir;
pumping the liquid sample into the cell culture chamber of a dendritic cell differentiation cassette of the system, whereby at least a portion of said monocytes bind to the monocyte binding substrate of the cell culture chamber; and
pumping a dendritic cell differentiation medium into the cell culture chamber, whereby at least a portion of the bound monocytes differentiate into dendritic cells and detach from the monocyte-binding substrate.

12. The method of claim 11, wherein the method further comprises pumping a dendritic cell maturation medium into the cell culture chamber to replace the dendritic cell differentiation medium, whereby at least a portion of the differentiated dendritic cells mature into mature dendritic cells.

13. The method of claim 11, wherein the method further comprises collecting mature dendritic cells from the cell culture chamber.

14. The method of claim 13, further comprising exposing the mature dendritic cells to one or more antigens.

15. The method of claim 11, wherein the mature dendritic cells have the phenotype Lin- and CD4+.

16. The method of claim 11, wherein the dendritic cell differentiation medium comprises IL4 and GM-CSF.

17. The method of claim 11, wherein said dendritic cell differentiation medium is pumped through the cell culture chamber continuously for about 2-6 days at a flow rate from about 1 µL/min to about 10 µL/min.

18. The method of claim 11, wherein the dendritic cell maturation medium comprises IL1β, IL6, TNFa, and PGE2.

19. The method of claim 18, wherein said dendritic cell maturation medium is pumped through the cell culture chamber continuously for about 1-3 days at a flow rate from about 1 µL/min to about 10 µL/min.

20. The method of claim 11, wherein dendritic cells from two or more subjects are prepared simultaneously.

* * * * *